(12) United States Patent
Buettelmann et al.

(10) Patent No.: US 7,153,874 B2
(45) Date of Patent: Dec. 26, 2006

(54) IMIDAZOLE DERIVATIVES

(75) Inventors: Bernd Buettelmann, Schopfheim (DE);
Simona Maria Ceccarelli, Basel (CH);
Georg Jaeschke, Basel (CH); Sabine Kolczewski, Rheinfelden (DE);
Richard Hugh Philip Porter, Reinach (CH); Eric Vieira, Allschwil (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 193 days.

(21) Appl. No.: 10/795,619

(22) Filed: Mar. 8, 2004

(65) Prior Publication Data
US 2004/0229917 A1 Nov. 18, 2004

(30) Foreign Application Priority Data
Mar. 10, 2003 (EP) .................................. 03004952

(51) Int. Cl.
*A61K 31/4439* (2006.01)
*A61K 31/4178* (2006.01)
*C07D 401/06* (2006.01)

(52) U.S. Cl. .................. 514/341; 546/272.7; 546/275.1
(58) Field of Classification Search ............. 546/272.7, 546/275.1; 514/341
See application file for complete search history.

(56) References Cited

U.S. PATENT DOCUMENTS

| 3,303,199 A | 2/1967 | Doebel et al. |
| 3,341,548 A | 9/1967 | Hoffer |
| 4,352,818 A | 10/1982 | Hunkeler et al. |
| 4,711,962 A | 12/1987 | Leone-Bay |
| 2004/0259917 A1* | 12/2004 | Cosford et al. ............. 514/341 |

FOREIGN PATENT DOCUMENTS

| DE | 2035905 | 2/1972 |
| EP | 059 390 | 9/1982 |
| EP | 0 304 910 A1 | 3/1989 |
| WO | WO 91/00277 | 1/1991 |
| WO | WO 99/02497 | 1/1999 |
| WO | WO 99/08678 | 2/1999 |
| WO | WO 01/16121 | 3/2001 |
| WO | WO 02/46166 | 6/2002 |

OTHER PUBLICATIONS

Sakamoto et al., Chem. Pharm. Bull., vol. 35(2) pp. 823-828 (1987).
Miller, et al., Chem. Mater., vol. 6(7) pp. 1023-1032 (1994).
Rapoport et al., Environ. Health Perspect. vol. 67, pp. 41-45 (1986).
Bond et al., Synth. Commun., vol. 19, pp. 2551-2566 (1989).
Sintas et al., Journal of Labelled Compds. & Radiopharmaceuticals, vol. 39, pp. 677-684 (1997).
Hoffer et al., J. Med. Chem., vol. 17(9) pp. 1019-1020 (1974).
Ohba et al. Chem. Pharm. Bull. vol. 42, pp. 1784-1790 (1994).
Kulkarni et al., Aust. J. Chem. vol. 40(8) pp. 1399-1413 (1987).
Vasileuskii et al., Bull. Acad. Sci. USSR Div. Chem. Sci. pp. 626-628 (1983).
Laronde et al., Inorg. Chim. Acta, vol. 296(1), pp. 208-221 (1999).
Shafiee et al., J. Heterocyclic Chem. vol. 33, pp. 671-673 (1996).
Shafiee et al., J. Heterocyclic Chem. vol. 35, pp. 607-610 (1998).
Ivanova et al. Chem. Heterocycl. Comp. vol. 36(2), pp. 262-264 (2000).
Wadsworth, G. H., J. Chem. Soc. vol. 57, p. 11 (1890).
Cornforth & Cookson, J. Chem. Soc. pp. 1085-1087 (1952).
Ross et al., J. Med. Chem. vol. 15(10) pp. 1035-1040 (1972).
Mutel, V., Expert Opin. Ther. Patents 12:12 (2002).
Kiyomori et al., Tetrahedron Lett. vol. 40: p. 2657-2660 (1999).
Tohda et al., Synthesis p. 777-778 (1977).
Cliff et al., Synthesis pp. 681-682 (1994).
Ohira, Synth. Comm. 19: pp. 561-564 (1989).
Collman et al., Org. Lett. 2: p. 1233-1236 (2000).
Schlaeger & Christensen, Cytotechnology 30:71-83 (1999).
Porter et al., Br. J. Pharmacol. 128: pp. 13-20 (1999).
Millan, Progress in Neurobiology 70: pp. 83-244 (2003).
Abstract corresponding to DE 2035905 (Document B6 above).
Arena, F. et al., Journal of Medicinal Chemistry, vol. 18, No. 11, pp. 1147-1150 (1975).

* cited by examiner

*Primary Examiner*—Patricia L. Morris
(74) *Attorney, Agent, or Firm*—George W. Johnston; Patricia S. Rocha-Tramaloni; Kimberly J. Prior

(57) ABSTRACT

The present invention provides 4-[1-Aryl-imidazol-4-yl-ethynyl]-2-alkyl-pyridine and 1-heteroaryl-imidazol-4-yl-ethynyl]-2-alkyl-pyridine derivatives and pharmaceutically acceptable salts thereof for the treatment or prevention of disorders mediated in full or in part by metabotropic glutamate receptor 5. These disorders include, e.g. acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases, such as schizophrenia and anxiety, depression, pain and drug dependency.

27 Claims, No Drawings

IMIDAZOLE DERIVATIVES

FIELD OF THE INVENTION

The present invention relates to metabotropic glutamate receptor 5 antagonists and treatment of mGluR5 mediated diseases.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by by-pass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, drug abuse/dependence such as nicotine addiction, opiate addiction, and alcohol abuse, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency [Expert Opin. Ther. Patents 12:12 (2002)].

Selective mGluR5 antagonists are especially useful for the treatment of anxiety and pain.

SUMMARY OF THE INVENTION

The present invention relates to novel imidazole derivatives, to processes for their production, to pharmaceutical compositions containing them, and to methods of treating or preventing mGluR5 mediated diseases.

More particularly the present invention provides in a first aspect novel 4-[1-aryl and 1-heteroaryl-imidazol-4-ylethynyl]-2-alkyl-pyridine derivatives as well as pharmaceutically acceptable salts thereof.

More particularly the present invention provides a compound of formula I

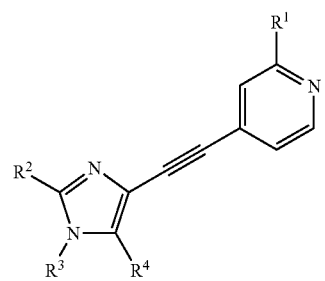

wherein
$R^1$ is $C_1$–$C_6$alkyl;
$R^2$ is $C_1$–$C_6$alkyl or $C_3$–$C_{12}$cycloalkyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamion, $C_3$–$C_{12}$cycloalkylamino, benzylamino and cyano; and
$R^4$ is hydrogen, C(O)H or $CH_2R^5$ wherein $R^5$ is hydrogen, OH, $C_1$–$C_6$alkyl or $C_3$–$C_{12}$cycloalkyl.

In one embodiment the present invention provides a compound of formula I*

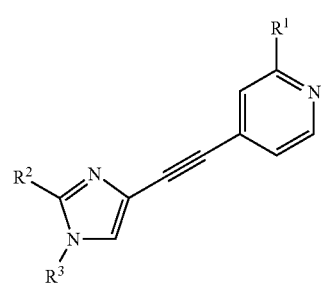

wherein
$R^1$ is lower alkyl;
$R^2$ is lower alkyl;
$R^3$ is aryl or heteroaryl, optionally substituted, by one, two or three substituents, selected from the group consisting of halogen, lower alkyl, lower alkyl-halogen and cyano;
or a pharmaceutically acceptable salt thereof.

It has now surprisingly been found that the compounds of general formula I are metabotropic glutamate receptor 5 antagonists. They have valuable therapeutic properties and can be used in the treatment or prevention of mGluR5 receptor mediated disorders. Thus, in another aspect, the present invention provides pharmaceutical compositions containing compounds of the invention and methods for treating or preventing mGluR5 receptor mediated disorders.

In a further aspect, the present invention provides methods for the manufacture of compounds of formula I.

DETAILED DESCRIPTION OF THE INVENTION

The following definitions of general terms used in the present description apply irrespective of whether the terms in question appear alone or in combination.

The term "lower alkyl" used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The term "cycloalkyl" used in the present description denotes cyclic saturated hydrocarbon residues with 3 to 12 carbon atoms. Examples for cycloalkyl include cyclopropyl, cyclobutyl and cyclopentyl.

The term "lower alkoxy" denotes a group wherein the alkyl residue is as defined above, and which is attached via an oxygen atom. Examples for $C_1$–$C_6$alkoxy include methoxy, methoxyethyl and methoxyethoxy. Examples for halogenmethoxy include trifluoromethoxy.

The term "$C_2$–$C_{11}$ heterocycloalkyl" refers to a nonaromatic group containing one individual ring, or one or more fused rings having from two to eleven carbon atoms in which at least one ring contains one or more heteroatoms selected from N, O, and S. Examples for $C_2$–$C_{11}$ heterocycloalkyl include pyrrolidinyl, morpholinyl and thiomorpholinyl.

The term "alkylamino" denotes an amine group, $NH_2$, in which one of the hydrogen atoms has been replaced with an alkyl residue or cycloalkyl residue as defined above. The term "dialkylamino" denotes an amine group in which both of the hydrogen atoms have been replaced with an alkyl residue or cycloalkyl residue as defined above. The two alkyl groups attached to the nitrogen atom can be the same or different. Examples for $C_1$–$C_6$alkylamino include methylamino and ethylamino. Examples for di-$C_1$–$C_6$alkylamino include dimethylamino.

Examples for $C_1$–$C_6$alkoxyamino include methoxyethylamino. Examples for ($C_1$–$C_6$alkoxy) $C_1$–$C_6$alkylamino include (methoxyethyl)methylamino. Examples for methoxycycloalkylamino include cyclopropylamino.

The term "halogen" denotes fluorine, chlorine, bromine and iodine.

"Aryl" represents an aromatic carbocyclic group consisting of one individual ring, or one or more fused rings in which at least one ring is aromatic in nature. Examples for aryl include phenyl. Examples for substituted aryl include fluorophenyl, difluorophenyl, chlorophenyl, dichlorophenyl, chlorofluorophenyl, cyanophenyl, methylphenyl, methoxyphenyl, fluoromethylphenyl, trifluoromethylphenyl and trifluoromethoxyphenyl.

The term "heteroaryl" refers to an aromatic 5- or 6-membered ring or one or more fused rings containing one or more heteroatoms selected from nitrogen, oxygen or sulphur. Examples of such heteroaryl groups are pyrimidinyl, pyrazinyl, pyridazinyl, pyridinyl and indolyl, e.g. pyridin-4-yl, pyridin-2-yl, pyrazin-2-yl and pyrimidin-2-yl. Examples for substituted heteroaryl include methylpyrimidinyl, dimethylpyrimidinyl, trifluoromethylpyrimidinyl, methoxypyrimidinyl, methoxyethoxypyrimidinyl, ethylpyrimidinyl, fluoropyrimidinyl, chloropyrimidinyl, bromopyrimidinyl, methylsulfanylpyrimidinyl, cyclopropylpyrimidinyl, methylpyrazinyl, cyclopropylpyrazinyl, chloropyrazinyl, methoxypyrazinyl, methoxyethoxypyrazinyl, methylaminopyrazinyl, dimethylaminopyrazinyl, cyclopropylaminopyrazinyl, morpholinylpyrazinyl, fluoropyridinyl, chloropyridinyl, bromopyridinyl, iodopyridinyl, methylpyridinyl, trifluoromethylpyridinyl, trifluoromethylmethylpyridinyl, cyclopropylpyridinyl, butylpyridinyl, methoxypyridinyl, dimethylaminopyridinyl, methylaminopyridinyl, ethylaminopyridinyl, pyrrolidinylpyridinyl, morpholinylpyridinyl, thiomorpholinylpyridinyl, (methoxyethyl)methylaminopyridinyl, methoxyethylaminopyridinyl, benzylaminopyridinyl and methyl-1H-indolyl.

The term "pharmaceutically acceptable salt" refers to any salt derived from an inorganic or organic acid.

"Pharmaceutically acceptable salts" of a compound means salts that are pharmaceutically acceptable, which are generally safe, non-toxic, and neither biologically nor otherwise undesirable, and that possess the desired pharmacological activity of the parent compound. These salts are derived from an inorganic or organic acid. If possible, compounds of formula I may be converted into pharmaceutically acceptable salts.

It should be understood that all references to pharmaceutically acceptable salts include solvent addition forms (solvates) or crystal forms (polymorphs) of the same acid addition salt.

Examples for pharmaceutically acceptable acid addition salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene-sulfonic acid, trimethylacetic acid, trifluoroacetic acid, and the like.

The terms "therapeutically inert carrier" and "pharmaceutically acceptable carrier" are used synonymously herein and mean a carrier or excipient that is pharmacologically acceptable, has no therapeutic activity and is substantially non-toxic to the subject to which the particular compound is administered.

"Therapeutically effective amount" means an amount that is effective to prevent, alleviate, or ameliorate symptoms of disease or prolong the survival of the subject being treated.

The present invention relates to novel imidazole derivatives, to processes for their production, their use as pharmaceuticals and to pharmaceutical compositions comprising them. More particularly the present invention provides in a first aspect novel 4-[1-aryl and 1-heteroaryl-imidazol-4-ylethynyl]-2-alkyl-pyridine derivatives as well as pharmaceutically acceptable salts thereof.

More particularly the present invention provides a compound of formula I

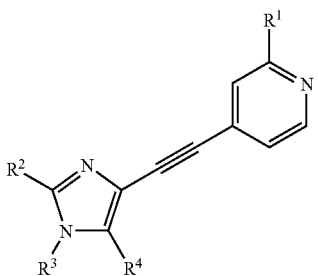

(I)

wherein
$R^1$ is $C_1$–$C_6$alkyl;
$R^2$ is $C_1$–$C_6$alkyl or $C_3$–$C_{12}$cycloalkyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino, benzylamino and cyano; and
$R^4$ is hydrogen, C(O)H or $CH_2R^5$ wherein $R^5$ is hydrogen, OH, $C_1$–$C_6$alkyl or $C_3$–$C_{12}$cycloalkyl.

In one embodiment the present invention provides a compound of formula I*

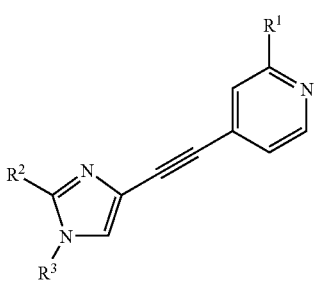

(I*)

wherein
$R^1$ is lower alkyl;
$R^2$ is lower alkyl;
$R^3$ is aryl or heteroaryl, optionally substituted, by one, two or three substituents, selected from the group consisting of halogen, lower alkyl, lower alkyl-halogen and cyano;

or a pharmaceutically acceptable salt thereof.

Preferred compounds of formula I* are those, in which $R^1$ and $R^2$ are both methyl.

Especially preferred are those compounds from this group, in which $R^3$ is substituted phenyl, wherein the substitution is fluoro, chloro, cyano or $CF_3$.

The following are examples of compounds, wherein the substitution is fluoro or chloro:
4-[1-(4-fluoro-phenyl)-2-methyl-1H-imidazol-4-ylethynyl]-2-methyl-pyridine,
4-[1-(3,4-dichloro-phenyl)-2-methyl-1H-imidazol-4-ylethynyl]-2-methyl-pyridine, HCl
4-[1-(2,4-difluoro-phenyl)-2-methyl-1H-imidazol-4-ylethynyl]-2-methyl-pyridine, or
4-[1-(3,4-difluoro-phenyl)-2-methyl-1H-imidazol-4-ylethynyl]-2-methyl-pyridine.

Examples of compounds, wherein the substitution is cyano, are as follows:
4-[2-methyl-4-(2-methyl-pyridin-4-ylethynyl)-imidazol-1-yl]-benzonitrile, or
3-[2-methyl-4-(2-methyl-pyridin-4-ylethynyl)-imidazol-1-yl]-benzonitrile.

The following is an example of compounds, wherein the substitution is $CF_3$:
2-methyl-4-[2-methyl-1-(3-trifluoromethyl-phenyl)-1H-imidazol-4-ylethynyl]-pyridine.

Especially preferred are further those compounds, wherein $R^1$ and $R^2$ are both methyl and $R^3$ is pyrimidinyl, for example the following compound:
2-[2-methyl-4-(2-methyl-pyridin-4-ylethynyl)-imidazol-1-yl]-pyrimidine.

In one embodiment the present invention provides a compound of formula I wherein $R^1$ is methyl, and $R^2$, $R^3$ and $R^4$ independently are as defined above or hereinafter.

In one embodiment the present invention provides a compound of formula I wherein $R^2$ is $C_1$–$C_6$alkyl. In another embodiment the present invention provides a compound of formula I wherein $R^2$ is methyl or isopropyl. In another embodiment the present invention provides a compound of formula I wherein $R^2$ is cyclopropyl. In all the above embodiments $R^1$, $R^3$ and $R^4$ independently are as defined above or hereinafter.

In one embodiment the present invention provides a compound of formula I wherein $R^3$ is unsubstituted aryl or aryl substituted by one, two or three substituents selected from halogen, $C_1$–$C_6$alkyl, S—$C_1$–$C_6$alkyl, $C_1$–$C_6$alkyl halogen, $C_1$–$C_6$alkoxy, halogen-$C_1$–$C_6$alkoxy, $C_3$–$C_{12}$cycloalkyl, $C_2$–$C_{11}$ heterocycloalkyl, $C_1$–$C_6$alkylamino, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino, benzylamino and cyano. In another embodiment $R^3$ is unsubstituted aryl or aryl substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_1$–$C_6$alkylamino, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino, and cyano. In yet another embodiment $R^3$ is unsubstituted aryl or aryl substituted by one, two or three substituents selected from $C_2$–$C_{11}$heterocycloalkyl. In a further embodiment, $R^3$ is unsubstituted aryl or aryl substituted by benzylamino.

In another embodiment the present invention provides a compound of formula I wherein $R^3$ is phenyl or phenyl substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano. In another embodiment the present invention provides a compound of formula I wherein $R^3$ is phenyl or phenyl substituted by one or two substituents selected from halogen, $C_1$–$C_6$alkyl, $C_1$–$C_6$alkyl-halogen, $C_1$–$C_6$alkoxy, halogen-$C_1$–$C_6$alkoxy and cyano. In another embodiment the present invention provides a compound of formula I wherein $R^3$ is phenyl substituted by one or two substituents selected from halogen, $C_1$–$C_6$alkyl, $C_1$–$C_6$alkyl-halogen, $C_1$–$C_6$alkoxy, halogen-$C_1$–$C_6$alkoxy and cyano. In another embodiment the present invention provides a compound of formula I wherein $R^3$ is phenyl substituted by one or two substituents selected from fluoro, chloro, methyl, trifluoromethyl, methoxy, trifluoromethoxy and cyano. In another embodiment the present invention provides a compound of formula I wherein $R^3$ is fluorophenyl, difluorophenyl, chlorophenyl, dichlorophenyl, cyanophenyl, trifluoromethylphenyl, fluoro-methylphenyl, chloro-fluorophenyl, methylphenyl, methoxyphenyl or trifluoromethoxyphenyl.

In all the above embodiments $R^1$, $R^2$ and $R^4$ independently are as defined above or hereinafter.

In one embodiment the present invention provides a compound of formula I wherein $R^3$ is unsubstituted heteroaryl or heteroaryl substituted by one, two or three substituents selected from the group consisting of halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino, benzylamino and cyano. In another embodiment, $R^3$ is unsubstituted heteroaryl or heteroaryl substituted by one, two or three substituents selected from the group consisting of halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalky, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino, and cyano. In yet another embodiment, $R^3$ is unsubstituted heteroaryl or heteroaryl substituted by one, two or three substituents selected from the group consisting of $C_2$–$C_{11}$heterocycloalkyl. In a further embodiment, $R^3$ is unsubstituted heteroaryl or heteroaryl substituted by benzylamino.

In another embodiment the present invention provides a compound of formula I wherein $R^3$ is unsubstituted pyrimidinyl, unsubstituted pyrazinyl or unsubstituted pyridinyl. In another embodiment the present invention provides a compound of formula I wherein $R^3$ is heteroaryl selected from pyrimidinyl, pyrazinyl, pyridinyl and indolyl wherein the heteroaryl is substituted by one or two substituents selected from halogen, $C_1$–$C_6$alkyl, S—$C_1$–$C_6$alkyl, $C_1$–$C_6$alkyl-halogen, $C_1$–$C_6$alkoxy, $C_3$–$C_{12}$cycloalkyl, $C_2$–$C_{11}$ heterocycloalkyl, $C_1$–$C_6$alkylamino, di-$C_1$–$C_6$alkylamino, $C_1$–$C_6$alkoxyamino, ($C_1$–$C_6$alkoxy)$C_1$–$C_6$alkylamino, $C_3$–$C_{12}$cycloalkylamino and benzylamino. In another embodiment the present invention provides a compound of formula I wherein $R^3$ is pyrimidinyl substituted by one or two substituents selected from halogen, $C_1$–$C_6$alkyl, S—$C_1$–$C_6$alkyl, $C_1$–$C_6$alkyl-halogen, $C_1$–$C_6$alkoxy and $C_3$–$C_{12}$cycloalkyl; or pyrazinyl substituted by one substituent selected from halogen, $C_1$–$C_6$alkyl, $C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino and $C_3$–$C_{12}$cycloalkylamino; or pyridinyl substituted by one or two substituents selected from halogen, $C_1$–$C_6$alkyl, $C_1$–$C_6$alkyl-halogen, $C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino and benzylamino; or methyl-1H-indolyl. In another embodiment the present invention provides a compound of formula I wherein $R^3$ is methylpyrimidinyl, ethylpyrimidinyl, dimethylpyrimidinyl, trifluoromethylpyrimidinyl, methoxypyrimidinyl, methoxyethoxypyrimidinyl, fluoropyrimidinyl, chloropyrimidinyl, bromopyrimidinyl, methylsulfanylpyrimidinyl, cyclopropylpyrimidinyl, methylpyrazinyl, cyclopropylpyrazinyl, methoxypyrazinyl, chloropyrazinyl, methylaminopyrazinyl, dimethylaminopyrazinyl, cyclopropylpyrazinyl, methylpyridinyl, butylpyridinyl, fluoropyridinyl, chloropyridinyl, bromopyridinyl, iodopyridinyl, trifluoromethylpyridinyl, (trifluoromethyl)methylpyridinyl, cyclopropylpyridinyl, methoxypyridinyl, methoxyethoxypyrazinyl, methylaminopyridinyl, ethylaminopyridinyl, dimethylaminopyridinyl, pyrrolidinylpyridinyl, morpholinylpyridinyl, thiomorpholinylpyridinyl, (methoxyethyl)methylaminopyridinyl, methoxyethylaminopyridinyl, benzylaminopyridinyl or methyl-1H-indolyl. In all the above embodiments $R^1$, $R^2$ and $R^4$ independently are as defined above or hereinafter.

In one embodiment the present invention provides a compound of formula I wherein $R^4$ is hydrogen, C(O)H or $CH_3$. In another embodiment the present invention provides a compound of formula I wherein $R^4$ is hydrogen. In all the above embodiments $R^1$, $R^2$ and $R^3$ independently are as defined above or hereinafter.

In one embodiment the present invention provides a compound of formula I wherein $R^1$ is methyl;
$R^2$ is $C_1$–$C_6$alkyl or $C_3$–$C_{12}$cycloalkyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
$R^4$ is hydrogen, C(O)H or $CH_2R^5$ wherein $R^5$ is hydrogen, OH, $C_1$–$C_6$alkyl or $C_3$–$C_{12}$cycloalkyl.

In another embodiment the present invention provides a compound of formula I wherein $R^1$ is methyl;
$R^2$ is methyl, isopropyl or cyclopropyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
$R^4$ is hydrogen, C(O)H or $CH_2R^5$ wherein $R^5$ is hydrogen, OH, $C_1$–$C_6$alkyl or $C_3$–$C_{12}$cycloalkyl.

In still another embodiment the present invention provides a compound of formula I wherein $R^1$ is methyl;
$R^2$ is methyl, isopropyl or cyclopropyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
$R^4$ is hydrogen, C(O)H or methyl.

In still another embodiment the present invention provides a compound of formula I wherein $R^1$ is methyl;
$R^2$ is methyl, isopropyl or cyclopropyl;
$R^3$ is aryl or heteroaryl, wherein the aryl or heteroaryl is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen- C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and R$^4$ is hydrogen.

In still another embodiment the present invention provides a compound of formula I wherein R$^1$ and R$^2$ are methyl;

R$^3$ is aryl or heteroaryl, wherein the aryl or heteroaryl is unsubstituted or substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and R$^4$ is hydrogen.

In still another embodiment the present invention provides a compound of formula I wherein R$^1$ and R$^2$ are methyl;

R$^3$ is unsubstituted aryl or aryl substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and R$^4$ is hydrogen.

In still another embodiment the present invention provides a compound of formula I wherein R$^1$ and R$^2$ are methyl;

R$^3$ is phenyl or phenyl substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and R$^4$ is hydrogen.

In still another embodiment the present invention provides a compound of formula I wherein R$^1$ and R$^2$ are methyl;

R$^3$ is phenyl or phenyl substituted by one or two substituents selected from halogen, C$_1$–C$_6$alkyl, C$_1$–C$_6$alkyl-halogen, C$_1$–C$_6$alkoxy, halogen-C$_1$–C$_6$alkoxy and cyano; and R$^4$ is hydrogen.

In still another embodiment the present invention provides a compound of formula I wherein R$^1$ and R$^2$ are methyl;

R$^3$ is phenyl substituted by one or two substituents selected from fluoro, chloro, methyl, trifluoromethyl, methoxy, trifluoromethoxy and cyano; and R$^4$ is hydrogen.

In still another embodiment the present invention provides a compound of formula I wherein R$^1$ and R$^2$ are methyl;

R$^3$ is fluorophenyl, difluorophenyl, chlorophenyl, dichlorophenyl, cyanophenyl, trifluoromethylphenyl, fluoromethylphenyl, chloro-fluorophenyl, methylphenyl, methoxyphenyl or trifluoromethoxyphenyl; and R$^4$ is hydrogen.

In still another embodiment the present invention provides a compound of formula I wherein R$^1$ and R$^2$ are methyl;

R$^3$ is unsubstituted heteroaryl or heteroaryl substituted by one, two or three substituents selected from the group consisting of halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C12cycloalkylamino, benzylamino and cyano; and R$^4$ is hydrogen.

In still another embodiment the present invention provides a compound of formula I wherein R$^1$ and R$^2$ are methyl;

R$^3$ is unsubstituted pyrimidinyl, unsubstituted pyrazinyl or unsubstituted pyridinyl; and R$^4$ is hydrogen.

In still another embodiment the present invention provides a compound of formula I wherein R$^1$ and R$^2$ are methyl;

R$^3$ is heteroaryl selected from pyrimidinyl, pyrazinyl, pyridinyl and indolyl wherein the heteroaryl is substituted by one or two substituents selected from halogen, C$_1$–C$_6$alkyl, S—C$_1$–C$_6$alkyl, C$_1$–C$_6$alkyl-halogen, C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino and benzylamino; and R$^4$ is hydrogen.

In still another embodiment the present invention provides a compound of formula I wherein R$^1$ and R$^2$ are methyl;

R$^3$ is pyrimidinyl substituted by one or two substituents selected from halogen, C$_1$–C$_6$alkyl, S—C$_1$–C$_6$alkyl, C$_1$–C$_6$alkyl-halogen, C$_1$–C$_6$alkoxy and C$_3$–C$_{12}$cycloalkyl; or pyrazinyl substituted by one substituent selected from halogen, C$_1$–C$_6$alkyl, C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino and C$_3$–C$_{12}$cycloalkylamino; or pyridinyl substituted by one or two substituents selected from halogen, C$_1$–C$_6$alkyl, C$_1$–C$_6$alkyl-halogen, C$_1$–C$_6$alkoxy, C$_3$–C$_{12}$cycloalkyl, C$_2$–C$_{11}$heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino and benzylamino; or methyl-1H-indolyl; and R$^4$ is hydrogen.

In still another embodiment the present invention provides a compound of formula I wherein R$^1$ and R$^2$ are methyl;

R$^3$ is methylpyrimidinyl, ethylpyrimidinyl, dimethylpyrimidinyl, trifluoromethylpyrimidinyl, methoxypyrimidinyl, methoxyethoxypyrimidinyl, fluoropyrimidinyl, chloropyrimidinyl, bromopyrimidinyl, methylsulfanylpyrimidinyl, cyclopropylpyrimidinyl, methylpyrazinyl, cyclopropylpyrazinyl, methoxypyrazinyl, chloropyrazinyl, methylaminopyrazinyl, dimethylaminopyrazinyl, cyclopropylpyrazinyl, methylpyridinyl, butylpyridinyl, fluoropyridinyl, chloropyridinyl, bromopyridinyl, iodopyridinyl, trifluoromethylpyridinyl, (trifluoromethyl) methylpyridinyl, cyclopropylpyridinyl, methoxypyridinyl, methoxyethoxypyrazinyl, methylaminopyridinyl, ethylaminopyridinyl, dimethylaminopyridinyl, pyrrolidinylpyridinyl, morpholinylpyridinyl, thiomorpholinylpyridinyl, (methoxyethyl)methylaminopyridinyl, methoxyethylaminopyridinyl, benzylaminopyridinyl or methyl-1H-indolyl; and $R^4$ is hydrogen.

Examples of compounds of formula I include
4-[1-(4-fluoro-phenyl)-2-methyl-1H-imidazol-4-ylethynyl]-2-methyl-pyridine,
4-[1-(3,4-dichloro-phenyl)-2-methyl-1H-imidazol-4-ylethynyl]-2-methyl-pyridine hydrochloride,
4-[1-(2,4-difluoro-phenyl)-2-methyl-1H-imidazol-4-ylethynyl]-2-methyl-pyridine,
4-[1-(3,4-difluoro-phenyl)-2-methyl-1H-imidazol-4-ylethynyl]-2-methyl-pyridine,
4-[2-methyl-4-(2-methyl-pyridin-4-ylethynyl)-imidazol-1-yl]-benzonitrile,
3-[2-methyl-4-(2-methyl-pyridin-4-ylethynyl)-imidazol-1-yl]-benzonitrile,
2-methyl-4-[2-methyl-1-(3-trifluoromethyl-phenyl)-1H-imidazol-4-ylethynyl]-pyridine,
2-[2-methyl-4-(2-methyl-pyridin-4-ylethynyl)-imidazol-1-yl]-pyrimidine,
4-[1-(4-chloro-phenyl)-2-methyl-1H-imidazol-4-ylethynyl]-2-methyl-pyridine,
4-[2-cyclopropyl-1-(4-fluoro-phenyl)-1H-imidazol-4-ylethynyl]-2-methyl-pyridine,
4-[1-(3-fluoro-phenyl)-2-methyl-1H-imidazol-4-ylethynyl]-2-methyl-pyridine,
4-[1-(3,5-difluoro-phenyl)-2-methyl-1H-imidazol-4-ylethynyl]-2-methyl-pyridine,
4-[1-(3-fluoro-4-methyl-phenyl)-2-methyl-1H-imidazol-4-ylethynyl]-2-methyl-pyridine,
4-[1-(3-chloro-4-fluoro-phenyl)-2-methyl-1H-imidazol-4-ylethynyl]-2-methyl-pyridine,
2-methyl-4-(2-methyl-1-p-tolyl-1H-imidazol-4-ylethynyl)-pyridine,
4-[1-(4-methoxy-phenyl)-2-methyl-1H-imidazol-4-ylethynyl]-2-methyl-pyridine,
2-methyl-4-[2-methyl-1-(4-trifluoromethyl-phenyl)-1H-imidazol-4-ylethynyl]-pyridine,
4,6-dimethyl-2-[2-methyl-4-(2-methyl-pyridin-4-ylethynyl)-imidazol-1-yl]-pyrimidine,
4-methyl-2-[2-methyl-4-(2-methyl-pyridin-4-ylethynyl)-imidazol-1-yl]-pyrimidine,
2-[2-methyl-4-(2-methyl-pyridin-4-ylethynyl)-imidazol-1-yl]-4-trifluoromethyl-pyrimidine,
4-methoxy-2-[2-methyl-4-(2-methyl-pyridin-4-ylethynyl)-imidazol-1-yl]-pyrimidine,
5-ethyl-2-[2-methyl-4-(2-methyl-pyridin-4-ylethynyl)-imidazol-1-yl]-pyrimidine,
5-fluoro-2-[2-methyl-4-(2-methyl-pyridin-4-ylethynyl)-imidazol-1-yl]-pyrimidine,
2-[2-methyl-4-(2-methyl-pyridin-4-ylethynyl)-imidazol-1-yl]-pyrazine,
2-methyl-5-[2-methyl-4-(2-methyl-pyridin-4-ylethynyl)-imidazol-1-yl]-pyrazine,
2-methyl-6-[2-methyl-4-(2-methyl-pyridin-4-ylethynyl)-imidazol-1-yl]-pyrazine,
2-cyclopropyl-6-[2-methyl-4-(2-methyl-pyridin-4-ylethynyl)-imidazol-1-yl]-pyrazine,
2-chloro-6-[2-methyl-4-(2-methyl-pyridin-4-ylethynyl)-imidazol-1-yl]-pyrazine,
2-methoxy-6-[2-methyl-4-(2-methyl-pyridin-4-ylethynyl)-imidazol-1-yl]-pyrazine,
2-chloro-4-[2-methyl-4-(2-methyl-pyridin-4-ylethynyl)-imidazol-1-yl]-pyrimidine,
4-chloro-2-[2-methyl-4-(2-methyl-pyridin-4-ylethynyl)-imidazol-1-yl]-pyrimidine,
4-[2-methyl-4-(2-methyl-pyridin-4-ylethynyl)-imidazol-1-yl]-2-methylsulfanyl-pyrimidine,
4-[2-methyl-4-(2-methyl-pyridin-4-ylethynyl)-imidazol-1-yl]-2-trifluoromethyl-pyrimidine,
2-[2-methyl-4-(2-methyl-pyridin-4-ylethynyl)-imidazol-1-yl]-pyridine,
6-fluoro-2-[2-methyl-4-(2-methyl-pyridin-4-ylethynyl)-imidazol-1-yl]-pyridine,
2-[2-methyl-4-(2-methyl-pyridin-4-ylethynyl)-imidazol-1-yl]-6-methylpyridine,
2-[2-isopropyl-4-(2-methyl-pyridin-4-ylethynyl)-imidazol-1-yl]-6-methylpyridine,
2-[2-methyl-4-(2-methyl-pyridin-4-ylethynyl)-imidazol-1-yl]-6-methyl-4-trifluoromethy-pyridine,
2-cyclopropyl-6-[2-methyl-4-(2-methyl-pyridin-4-ylethynyl)-imidazol-1-yl]-pyridine,
2-butyl-6-[2-methyl-4-(2-methyl-pyridin-4-ylethynyl)-imidazol-1-yl]-pyridine,
2-[2-methyl-4-(2-methyl-pyridin-4-ylethynyl)-imidazol-1-yl]-6-trifluoromethyl-pyridine,
2-[2-isopropyl-4-(2-methyl-pyridin-4-ylethynyl)-imidazol-1-yl]-6-trifluoromethyl-pyridine,
2-methoxy-6-[2-methyl-4-(2-methyl-pyridin-4-ylethynyl)-imidazol-1-yl]-pyridine,
2-[2-methyl-4-(2-methyl-pyridin-4-ylethynyl)-imidazol-1-yl]-5-methyl-pyridine,
2-[2-isopropyl-4-(2-methyl-pyridin-4-ylethynyl)-imidazol-1-yl]-5-methyl-pyridine,
5-chloro-2-[2-methyl-4-(2-methyl-pyridin-4-ylethynyl)-imidazol-1-yl]-pyridine,
5-bromo-2-[2-methyl-4-(2-methyl-pyridin-4-ylethynyl)-imidazol-1-yl]-pyridine,
4-iodo-2-[2-methyl-4-(2-methyl-pyridin-4-ylethynyl)-imidazol-1-yl]-pyridine,
2-[2-methyl-4-(2-methyl-pyridin-4-ylethynyl)-imidazol-1-yl]-4-methyl-pyridine,
2-[2-methyl-4-(2-methyl-pyridin-4-ylethynyl)-imidazol-1-yl]-4-trifluoromethyl-pyridine,
2-methoxy-4-[2-methyl-4-(2-methyl-pyridin-4-ylethynyl)-imidazol-1-yl]-pyridine,
2-chloro-5-[2-methyl-4-(2-methyl-pyridin-4-ylethynyl)-imidazol-1-yl]-pyridine,
2-bromo-5-[2-methyl-4-(2-methyl-pyridin-4-ylethynyl)-imidazol-1-yl]-pyridine,
5-[2-methyl-4-(2-methyl-pyridin-4-ylethynyl)-imidazol-1-yl]-2-methyl-pyridine,
2-cyclopropyl-5-[2-methyl-4-(2-methyl-pyridin-4-ylethynyl)-imidazol-1-yl]-pyridine,
2-butyl-5-[2-methyl-4-(2-methyl-pyridin-4-ylethynyl)-imidazol-1-yl]-pyridine,
3-fluoro-5-[2-methyl-4-(2-methyl-pyridin-4-ylethynyl)-imidazol-1-yl]-pyridine,
3-chloro-5-[2-methyl-4-(2-methyl-pyridin-4-ylethynyl)-imidazol-1-yl]-pyridine,
dimethyl-{5-[2-methyl-4-(2-methyl-pyridin-4-ylethynyl)-imidazol-1-yl]-pyridin-3-yl}-amine,
dimethyl-{6-[2-methyl-4-(2-methyl-pyridin-4-ylethynyl)-imidazol-1-yl]-pyridin-2-yl}-amine,
dimethyl-{6-[2-methyl-4-(2-methyl-pyridin-4-ylethynyl)-imidazol-1-yl]-pyrazin-2-yl}-amine,
ethyl-{5-[2-methyl-4-(2-methyl-pyridin-4-ylethynyl)-imidazol-1-yl]-pyridin-3-yl}-amine,
methyl-{6-[2-methyl-4-(2-methyl-pyridin-4-ylethynyl)-imidazol-1-yl]-pyridin-2-yl}-amine,
methyl-{6-[2-methyl-4-(2-methyl-pyridin-4-ylethynyl)-imidazol-1-yl]-pyrazin-2-yl}-amine, cyclopropyl-{6-[2-methyl-4-(2-methyl-pyridin-4-ylethynyl)-imidazol-1-yl]-pyrazin-2-yl}-amine,
1-{5-[2-methyl-4-(2-methyl-pyridin-4-ylethynyl)-imidazol-1-yl]-pyridin-3-yl}-amine,
1-{6-[2-methyl-4-(2-methyl-pyridin-4-ylethynyl)-imidazol-1-yl]-pyridin-2-yl}-pyrrolidine,
1-{3-[2-methyl-4-(2-methyl-pyridin-4-ylethynyl)-imidazol-1-yl]-pyridin-5-yl}-pyrrolidine,
4-{6-[2-methyl-4-(2-methyl-pyridin-4-ylethynyl)-imidazol-1-yl]-pyridin-2-yl}-morpholine,
4-{6-[2-methyl-4-(2-methyl-pyridin-4-ylethynyl)-imidazol-1-yl]-pyrazin-2-yl}-morpholine,
4-{6-[2-methyl-4-(2-methyl-pyridin-4-ylethynyl)-imidazol-1-yl]-pyridin-2-yl}-thiomorpholine,
(2-methoxy-ethyl)-methyl-{6-[2-methyl-4-(2-methyl-pyridin-4-ylethynyl)-imidazol-1-yl]-pyridin-2-yl}-amine,
(2-methoxy-ethyl)-{6-[2-methyl-4-(2-methyl-pyridin-4-ylethynyl)-imidazol-1-yl]-pyridin-2-yl}-amine,
4-cyclopropyl-2-[2-methyl-4-(2-methyl-pyridin-4-ylethynyl)-imidazol-1-yl]-pyridine,
5-cyclopropyl-2-[2-methyl-4-(2-methyl-pyridin-4-ylethynyl)-imidazol-1-yl]-pyridine,
4-fluoro-6-[2-methyl-4-(2-methyl-pyridin-4-ylethynyl)-imidazol-1-yl]-pyrimidine,
5-bromo-2-[2-methyl-4-(2-methyl-pyridin-4-ylethynyl)-imidazol-1-yl]-pyrimidine,
5-methyl-2-[2-methyl-4-(2-methyl-pyridin-4-ylethynyl)-imidazol-1-yl]-pyrimidine,
2-cyclopropyl-4-[2-methyl-4-(2-methyl-pyridin-4-ylethynyl)-imidazol-1-yl]-pyrimidine,
4-cyclopropyl-2-[2-methyl-4-(2-methyl-pyridin-4-ylethynyl)-imidazol-1-yl]-pyrimidine,
2-(2-methoxy-ethoxy)-6-[2-methyl-4-(2-methyl-pyridin-4-ylethynyl)-imidazol-1-yl]-pyrimidine,
2-(2-methoxy-ethoxy)-6-[2-methyl-4-(2-methyl-pyridin-4-ylethynyl)-imidazol-1-yl]-pyrimidine,
2-methyl-4-[2-methyl-1-(3-trifluoromethoxy-phenyl)-1H-imidazol-4-ylethynyl]-pyridine,
1-methyl-5-[2-methyl-4-(2-methyl-pyridin-4-ylethynyl)-imidazol-1-yl]-1H-indole,
benzyl-{5-[2-methyl-4-(2-methyl-pyridin-4-ylethynyl)-imidazol-1-yl]-pyridin-3-yl}-amine,
4-[1-(4-fluoro-phenyl)-2,5-dimethyl-1H-imidazol-4-ylethynyl]-2-methyl-pyridine and
3-(4-fluoro-phenyl)-2-methyl-5-(2-methyl-pyridin-4-yl-ethynyl)-3H-imidazole-4-carbaldehyde.

In one embodiment the present invention provides a compound of formula I selected from
4-[1-(4-fluoro-phenyl)-2-methyl-1H-imidazol-4-ylethynyl]-2-methyl-pyridine,
4-[1-(3,4-dichloro-phenyl)-2-methyl-1H-imidazol-4-ylethynyl]-2-methyl-pyridine hydrochloride,
4-[1-(2,4-difluoro-phenyl)-2-methyl-1H-imidazol-4-ylethynyl]-2-methyl-pyridine,
4-[1-(3,4-difluoro-phenyl)-2-methyl-1H-imidazol-4-ylethynyl]-2-methyl-pyridine,
4-[2-methyl-4-(2-methyl-pyridin-4-ylethynyl)-imidazol-1-yl]-benzonitrile,
3-[2-methyl-4-(2-methyl-pyridin-4-ylethynyl)-imidazol-1-yl]-benzonitrile,
2-methyl-4-[2-methyl-1-(3-trifluoromethyl-phenyl)-1H-imidazol-4-ylethynyl]-pyridine,
2-[2-methyl-4-(2-methyl-pyridin-4-ylethynyl)-imidazol-1-yl]-pyrimidine,
2-[2-methyl-4-(2-methyl-pyridin-4-ylethynyl)-imidazol-1-yl]-4-trifluoromethyl-pyrimidine,
4-methoxy-2-[2-methyl-4-(2-methyl-pyridin-4-ylethynyl)-imidazol-1-yl]-pyrimidine,
2-cyclopropyl-6-[2-methyl-4-(2-methyl-pyridin-4-ylethynyl)-imidazol-1-yl]-pyrazine,
4-chloro-2-[2-methyl-4-(2-methyl-pyridin-4-ylethynyl)-imidazol-1-yl]-pyrimidine,
2-cyclopropyl-6-[2-methyl-4-(2-methyl-pyridin-4-ylethynyl)-imidazol-1-yl]-pyridine,
2-methoxy-6-[2-methyl-4-(2-methyl-pyridin-4-ylethynyl)-imidazol-1-yl]-pyridine,
dimethyl-{6-[2-methyl-4-(2-methyl-pyridin-4-ylethynyl)-imidazol-1-yl]-pyridin-2-yl}-amine,
1-methyl-5-[2-methyl-4-(2-methyl-pyridin-4-ylethynyl)-imidazol-1-yl]-1H-indole,
4-[1-(4-fluoro-phenyl)-2,5-dimethyl-1H-imidazol-4-ylethynyl]-2-methyl-pyridine and
3-(4-fluoro-phenyl)-2-methyl-5-(2-methyl-pyridin-4-yl-ethynyl)-3H-imidazole-4-carbaldehyde.

The present invention also provides a process for the production of a compound of formula I

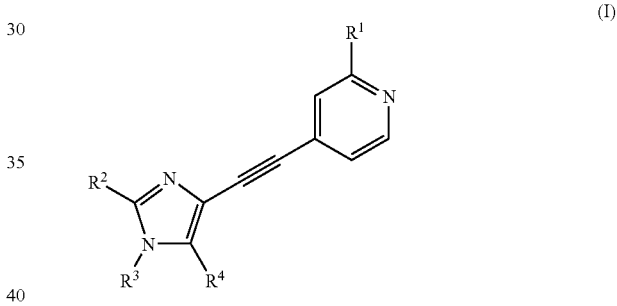

wherein $R^1$ is $C_1$–$C_6$alkyl;

$R^2$ is $C_1$–$C_6$alkyl or $C_3$–$C_{12}$cycloalkyl;

$R^3$ is unsubstituted aryl or aryl substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano, unsubstituted heteroaryl or heteroaryl substituted by one, two or three substituents selected from the group consisting of halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_2$–$C_{11}$heterocycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and $R^4$ is hydrogen, C(O)H or $CH_2R^5$ wherein $R^5$ is hydrogen, OH, $C_1$–$C_6$alkyl or $C_3$–$C_{12}$cycloalkyl;

which process comprises reacting (a) a compound of formula II

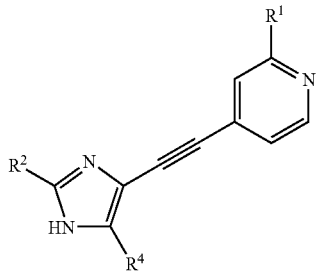

wherein $R^1$, $R^2$ and $R^4$ have the meanings as defined above, with a compound of formula III $$R^3\text{-}Z \qquad \text{(III)}$$

wherein $R^3$ has the meanings as defined above and Z is halogen or $B(OH)_2$; or (b) a compound of formula IV

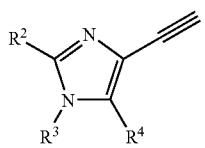

wherein $R^2$, $R^3$ and $R^4$ have the meanings as defined above, with a compound of formula V

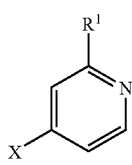

wherein $R^1$ has the meanings as defined above and X is halogen; or (c) a compound of formula VI

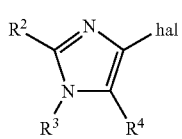

wherein $R^2$, $R^3$ and $R^4$ have the meanings as defined above and hal is halogen, with a compound of formula VII

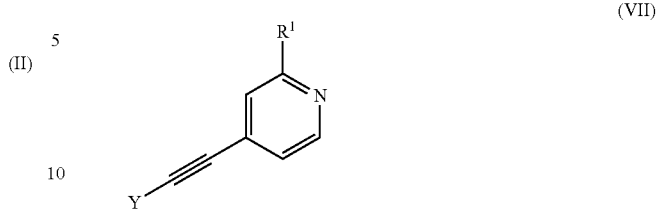

wherein $R^1$ has the meaning as defined above and Y is trimethylsilyl or hydrogen.

The reaction as described in (a) may be carried out in accordance with standard procedures, e.g. by arylation of a compound of formula II using an aromatic boronic acid and a copper catalyst in a solvent like dichloromethane or tetrahydrofurane [see e.g. Colmann et al., Org. Lett. 2:1233 (2000)] or by heating a compound of formula II and a compound of formula III wherein Z is halogen with a base like potassium carbonate or cesium carbonate in a solvent like dimethylformamide, or Pd catalyzed according to Buchwald conditions [see e.g. Example 8; Buchwald et al., Tetrahedron Lett. 40:2657 (1999)]. The reaction as described in (b) may be carried out by a Sonogashira coupling of a compound of formula IV and a compound of formula V in the presence of, e.g., CuI, $(Ph_3P)_2PdCl_2$, $Et_3N$ in a solvent like tetrahydrofuran or dimethylformamide [Sonogashira et al., Synthesis 777 (1977)]. In one embodiment the meaning X in compounds of formula V is bromine or iodine. The reaction as described in (c) above may, e.g. be carried out in the presence of CuI, $(Ph_3P)_2PdCl_2$, $Et_3N$, $n\text{-}Bu_4F$ in a solvent like tetrahydrofuran or dimethylformamide.

The salt forms are made by standard procedures known to the skilled artisan.

The compounds of formulae II, IV, VI and VII are novel and also an embodiment of the present invention.

The compounds of formulae III and V are commercially available or their preparation is known to the skilled artisan.

The compounds of formula II may be prepared by reacting a compound of formula VIII wherein $R^2$ and $R^4$ have the above meanings and hal is halogen, with a compound of formula VII as above.

The compounds of formula VIII may be prepared as described e.g. in Cliff and Pyne [Synthesis 681–682 (1994)].

The compounds of formula IV may be prepared by reacting a compound of formula IX

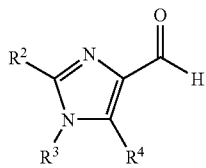
(IX)

wherein $R^2$, $R^3$ and $R^4$ have the meanings as defined above, with dimethyl (1-diazo-2-oxopropyl)phosphonate as described in Ohira [Synth.Comm. 19:561–564 (1989)].

Compounds of formula VI may be prepared by reacting a compound of formula VIII as above with a compound of formula X

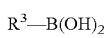 (X)

wherein $R^3$ has the meanings as defined above.

The reaction may take place by arylation of a compound of formula VIII using an aromatic boronic acid (compound of formula X) and a copper catalyst in a solvent like dichloromethane or tetrahydrofurane under an oxygen atmosphere [see e.g. Colmann et al., Org.Lett. 2:1233 (2000)].

Compounds of formula VII may be prepared by reacting a compound of formula V as above with a compound of formula XI

 (XI)

The reaction may take place by a Sonogashira coupling in the presence of eg. CuI, $(Ph_3P)_2PdCl_2$, $Et_3N$ in a solvent like tetrahydrofuran or dimethylformamide [Sonogashira et al., Synthesis 777 (1977)].

Compounds of formula IX may be prepared by oxidizing a compound of formula XII

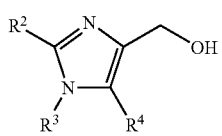 (XII)

according to methods known to the skilled artisan.

Compounds of formula XII may be prepared by deprotecting a compound of formula

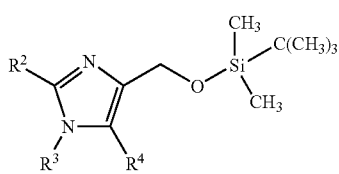 (XIII)

according to methods known to the skilled artisan.

Compounds of formula XIII may be prepared by alkylating a compound of formula XIV

 (XIV)

with an alkylating agent of formula XVa $R^2$-hal (XVa)

according to methods known to the skilled artisan.

Starting compounds of formula XVa are commercially available.

Compounds of formula XIV may be prepared by treating a compound of formula XV

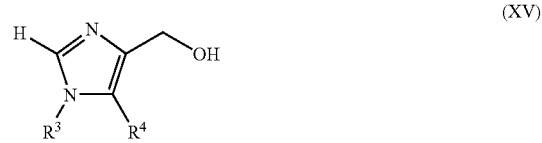 (XV)

with tert.-butyl dimethyl silyl chloride according to methods known to the skilled artisan.

Compounds of formula XV may be prepared by treating a compound of formula XVI

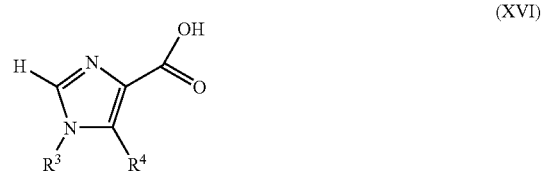 (XVI)

with a reducing agent according to methods known to the skilled artisan.

Compounds of formula XVI may be prepared by hydrolysing a compound of formula XVII

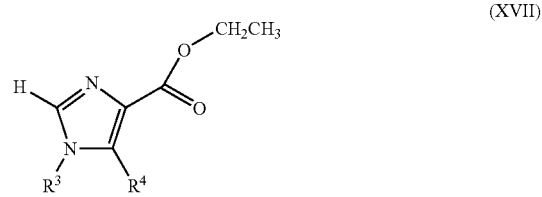 (XVII)

according to methods known to the skilled artisan.

Compounds of formula XVII may be prepared by treating a compound of formula XVIII $R^3$—$NH_2$ (XVIII)

with e.g. triethyl orthoformate, ethylnitro acetate, glacial acetic acid and iron powder according to methods known to the skilled artisan.

Compounds of formula XVIII are commercially available.
The compounds of general formula I* and their pharmaceutically acceptable salts can be manufactured by two general procedures, which procedures are outlined below for compounds wherein $R^1$ is methyl and $R^2$ is methyl, but which procedures are applicable for all compounds according to Formula I*.
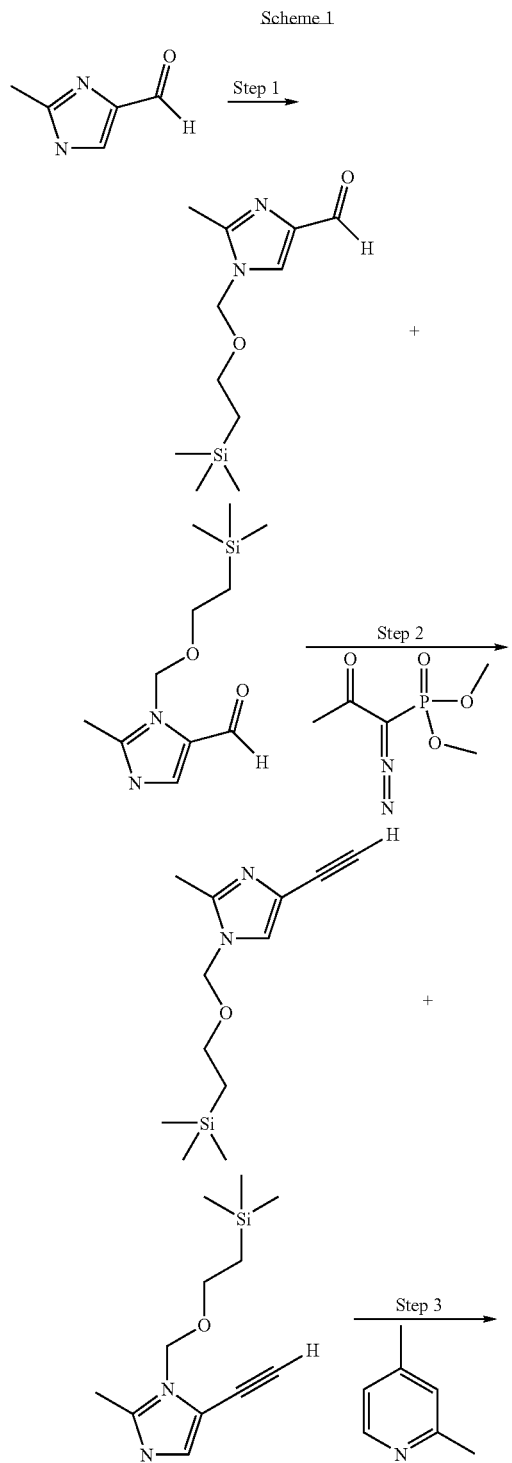
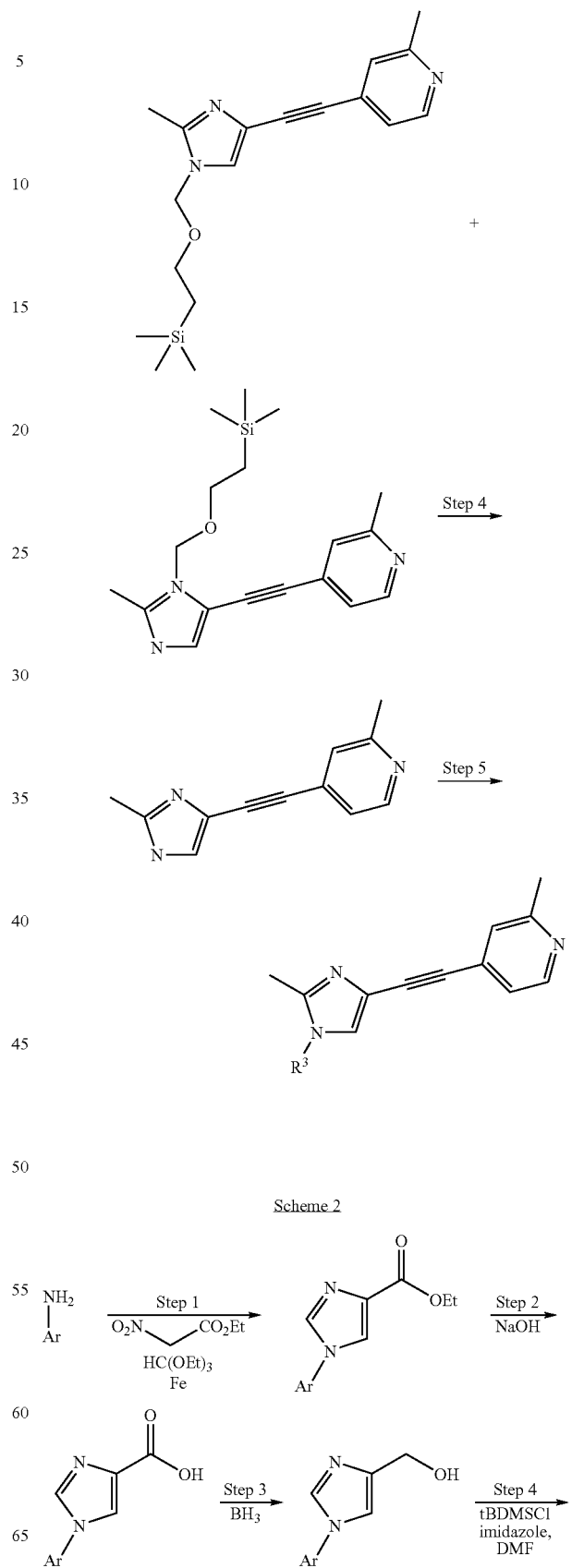

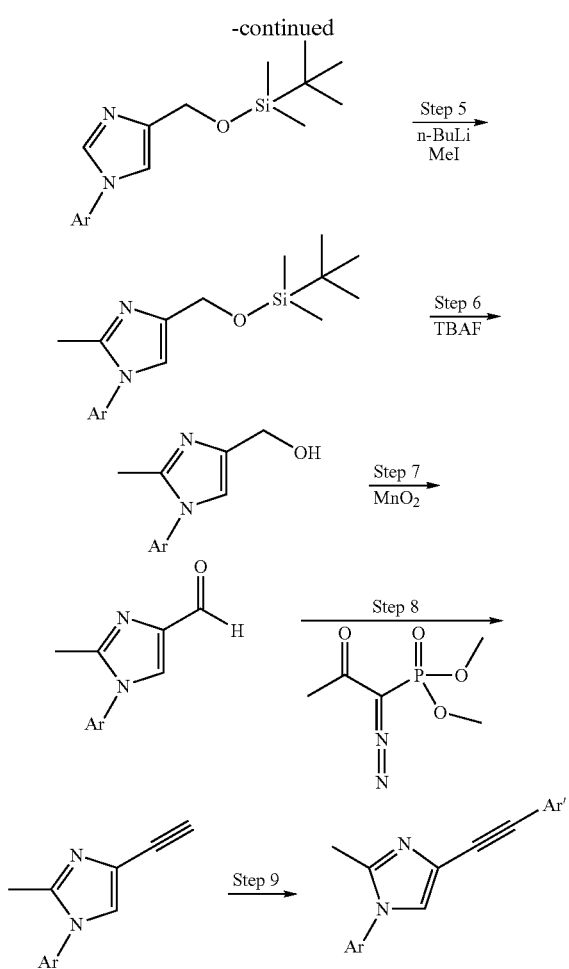

The invention also relates to a process for preparing a compound according to general formula I* following the general procedures as outlined above for compounds of formula I* wherein $R^1$ is methyl and $R^2$ is methyl ($R^3$ and $R^1$ are designated Ar and Ar', respectively, in Scheme 2).

Pharmaceutically acceptable salts of compounds of formula I can be manufactured readily according to methods known per se and taking into consideration the nature of the compound to be converted into a salt. Inorganic or organic acids such as, e.g., hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts (hereinafter: Pharmaceutical Compounds) are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

Pharmaceutical Compounds are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of Pharmaceutical Compounds was tested using the following method:

For binding experiments, cDNA encoding human mGlu 5a receptor was transiently transfected into EBNA cells using a procedure described by Schlaeger and Christensen [Cyto-technology 15:1–13 (1998)]. Cell membrane homogenates were stored at −80° C. until the day of assay where upon they were thawed and resuspended and polytronised in 15 mM Tris-HCl, 120 mM NaCl, 100 mM KCl, 25 mM $CaCl_2$, 25 mM $MgCl_2$ binding buffer at pH 7.4 to a final assay concentration of 20 μg protein/well.

Saturation isotherms were determined by addition of twelve [$^3$H]MPEP concentrations (0.04–100 nM) to these membranes (in a total volume of 200 μl) for 1 h at 4° C. Competition experiments were performed with a fixed concentration of [$^3$H]MPEP (2 nM) and $IC_{50}$ values of test compounds evaluated using 11 concentrations (0.3–10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S. A., Zürich, Switzerland) and shaking for 20 min.

For functional assays, [$Ca^{2+}$]i measurements were performed as described previously by Porter et al. [Br. J. Pharmacol. 128:13–20 (1999)] on recombinant human mGlu 5a receptors in HEK-293 cells. The cells were dye loaded using Fluo 4-AM (obtainable by FLUKA, 0.2 μM final concentration). [$Ca^{2+}$]i measurements were performed using a fluorometric imaging plate reader (FLIPR, Molecular Devices Corporation, La Jolla, Calif., USA). Antagonist evaluation was perfromed following a 5 min preincubation with the test compounds followed by the addition of a submaximal addition of agonist.

The inhibition (antagonists) curves were fitted with a four parameter logistic equation giving $IC_{50}$, and Hill coefficient using an iterative non linear curve fitting software (Xcel fit).

For binding experiments the Ki values of the compounds tested are given. The Ki value is defined by the following formula:

$$K_i = IC_{50}/[1+L/K_d]$$

in which the $IC_{50}$ values are those concentrations of the compounds tested which cause 50% inhibition of the competing radioligand ([$^3$H]MPEP). L is the concentration of radioligand used in the binding experiment and the $K_d$ value of the radioligand is empirically determined for each batch of membranes prepared.

Pharmaceutical Compounds are mGluR 5a receptor antagonists. The activities of Pharmaceutical Compounds as measured in the assay described above are in the range of $K_i$<150 nM.

Activity data

| Cpd no. | $K_i$ [nM] |
| --- | --- |
| 1 | 29 |
| 2 | 18 |
| 3 | 38 |
| 4 | 25 |
| 5 | 83 |
| 6 | 91 |
| 7 | 24 |
| 8 | 74 |
| 18 | 45 |
| 21 | 17 |
| 22 | 18 |
| 29 | 25 |
| 56 | 27 |
| 57 | 16 |
| 68 | 18 |
| 71 | 19 |
| 88 | 33 |
| 89 | 65 |

Ki (mGluR5)

Activity specifically as anxiolytic agents may be demonstrated in accordance with standard test methods, e.g. as described in the Vogel conflict drinking test [see e.g. review of Millan, Progress in Neurobiology 70:83–244 (2003)]:

The Vogel conflict drinking test is a procedure that has been widely used as a screening method for anxiolytics. In this procedure, the water intake of thirsty rats is measured under conditions where water intake is suppressed by electric shock. In our version of the test, rats are water-restricted for 23 h during three consecutive days. One day after the first water restriction, they are allowed to freely drink for one hour in their home-cage. The second day, they are allowed to lick from a drinking spout in the operant box for 15 min, after which they are allowed to freely drink in their home cage for one hour. On the third-test-day, they are allowed to lick again from a drinking spout for 10 min, but now they receive a 0.5 mA electric stimulus for 0.5 sec every sec that they lick (counted as an interruption of an infrared beam in front of the spout). The electric stimulus suppresses the time that the animals spend drinking, and treatment with Pharmaceutical Compounds partially or completely reinstates normal drinking duration. Pharmaceutical Compounds can be used as medicaments, e.g. in the form of pharmaceutical preparations. The pharmaceutical preparations can be administered orally, e.g. in the form of tablets, coated tablets, drágees, hard and soft gelatine capsules, solutions, emulsions or suspensions. However, the administration can also be effected rectally, e.g. in the form of suppositories, or parenterally, e.g. in the form of injection solutions.

The present invention also provides pharmaceutical compositions containing Pharmaceutical Compounds and a pharmaceutically inert, inorganic or organic carrier. Such pharmaceutical compositions can be in the form of tablets, coated tablets, drágees, hard and soft gelatine capsules, solutions, emulsions or suspensions. The pharmaceutical compositions also can be in the form of suppositories or injectable solutions. The invention further provides a process for preparation of such compositions, which comprises bringing one or more Pharmaceutical Compound and, if desired, one or more other therapeutically valuable substances into a galenical dosage form together with one or more therapeutically inert, pharmaceutically acceptable carriers.

Lactose, corn starch or derivatives thereof, talc, stearic acid or its salts and the like can be used, as carriers for tablets, coated tablets, drágees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

It has now surprisingly been found that the compounds of general formula I are metabotropic glutamate receptor 5 antagonists. Compounds of formula I are distinguished by having valuable therapeutic properties. They can be used in the treatment or prevention of mGluR5 receptor mediated disorders. Therefore, the invention further provides a method of treating or preventing an mGluR5 receptor mediated disorder which comprises administering to an individual a therapeutically effective amount of a Pharmaceutical Compound of the invention.

The dosage at which the Pharmaceutical Compounds can be administered can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The following examples are provided to further elucidate the invention:

Preparation of the starting compounds

EXAMPLE II-1

2-Methyl-4-(2-methyl-1H-imidazol-4-ylethynyl)-pyridine (II-1)

Method A1:

Step 1: 2-Methyl-1-(2-trimethylsilanyl-ethoxymethyl)-1H-imidazole-4-carbaldehyde and 2-methyl-3-(2-trimethylsilanyl-ethoxymethyl)-3H-imidazole-4-carbaldehyde A solution of 2-methyl-1H-imidazol-4-carbaldehyde (5.0 g, 45 mmol) in 125 mL dry DMF was added dropwise at 0° C.

to suspension of sodium hydride (1.98 g, 45 mmol) in dry DMF. The reaction mixture was stirred at RT for 2 h. A solution of 2-(trimethylsilyl)ethoxymethyl chloride (7.97 g, 45 mmol) in 50 mL dry THF was added dropwise at 0° C. The reaction mixture was stirred at RT overnight. Water (100 mL) was added carefully and the solvents were evaporated. The residue was taken up in 150 mL water and extracted three times with ethyl acetate (150 mL each). The combined organic extracts were dried with sodium sulfate, filtered and evaporated. The crude product (mixture of 2 isomers, 12.5 g) was used without any further purification for the next step, MS: m/e=241.2 (M+H$^+$).

Step 2: 4-Ethynyl-2-methyl-1-(2-trimethylsilanyl-ethoxymethyl)-1H-imidazole and 5-ethynyl-2-methyl-1-(2-trimethylsilanyl-ethoxymethyl)-1H-imidazole(1-Diazo-2-oxo-propyl)-phosphonic acid dimethyl ester (10.4 g, 54 mmol) was dissolved in 150 mL methanol. Potassium carbonate (12.6 g, 90 mmol) was added. A solution of crude 2-methyl-1-(2-trimethylsilanyl-ethoxymethyl)-1H-imidazole-4-carbaldehyde and 2-methyl-3-(2-trimethylsilanyl-ethoxymethyl)-3H-imidazole-4-carbaldehyde (45 mmol) in 150 mmol methanol was added dropwise at RT. The reaction mixture was stirred at RT overnight. The solvent was evaporated. The residue was taken up in 150 mL water and extracted three times with ethyl acetate (150 mL each). The combined organic extracts were dried with sodium sulfate, filtered and evaporated. The crude product was purified by column chromatography on silica gel (cyclohexane/ethyl acetate 1:1) and the desired compound was obtained as a mixture of 2 isomers (8.36 g, 78%), MS: m/e=237.0 (M+H$^+$).

Step 3: 2-Methyl-4-[2-methyl-1-(2-trimethylsilanyl-ethoxymethyl)-1H-imidazol-4-yl-ethynyl]-pyridine and 2-methyl-4-[2-methyl-3-(2-trimethylsilanyl-ethoxymethyl)-3H-imidazol-4-ylethynyl]-pyridine 4-Bromo-2-methyl-pyridine (1.92 g, 11.2 mmol) was dissolved in 50 mL dry THF and triethylamine (3.9 mL, 30 mmol) was added. This mixture was evacuated and backfilled with argon several times to remove oxygen from the solution. Triphenylphosphin (73 mg, 0.28 mmol) and bis(triphenylphosphin)palladium(II)chloride (327 mg, 0.47 mmol) were added and the reaction mixture was stirred at RT for 20 min. Copper(I)iodide (53 mg, 0.28 mmol) and a mixture of 4-ethynyl-2-methyl-1-(2-trimethylsilanyl-ethoxymethyl)-1H-imidazole and 5-ethynyl-2-methyl-1-(2-trimethyl-silanyl-ethoxymethyl)-1H-imidazole (2.2 g, 9.3 mmol) were added. The reaction mixture was then stirred at RT overnight. The solvent was evaporated. The residue was taken up in 50 mL water and extracted three times with ethyl acetate (70 mL each). The combined organic extracts were dried with sodium sulfate, filtered and evaporated. The crude product was purified by flash chromatography on silica gel (heptane/ethyl acetate 80:20 →0:100 gradient ) and the desired compound was obtained as a mixture of 2 isomers (2.86 g, 94%), MS: m/e=327.2 (M$^+$).

Step 4: 2-Methyl-4-(2-methyl-1H-imidazol-4-ylethynyl)-pyridine

2-Methyl-4-[2-methyl-1-(2-trimethylsilanyl-ethoxymethyl)-1H-imidazol-4-ylethynyl]-pyridine and 2-methyl-4-[2-methyl-3-(2-trimethylsilanyl-ethoxymethyl)-3H-imidazol-4-ylethynyl]-pyridine (2.85 g, 8.7 mmol) were dissolved in 50 mL EtOH saturated with HCl. The reaction mixture was stirred at RT overnight. The solvent was evaporated. The residue was taken up in 50 mL water and adjusted to pH7 by addition of sodium hydroxide. The aqueous phase was extracted three times with ethyl acetate (70 mL each). The combined organic extracts were dried with magnesium sulfate, filtered and evaporated. The crude product was purified by flash chromatography on silica gel (methylene chloride/methanol 100:5→85:15 gradient) and the desired compound was obtained as an off-white foam (1.19 g, 69%), MS: m/e=198.2 (M+H$^+$).

Method A2:

Step 1: 4-Iodo-2-methyl-pyridine

4-Chloropicoline (10 g, 78 mmol), sodium iodide (17.8 g, 118 mmol) and hydroiodic acid (57%, 26 mL, 196 mmol) were heated in a sealed class tube at 140° C. for 7 days. The reaction mixture was poured into ice water and neutralized by addition of sodium hydroxide. This mixture was extracted three times with dichloromethane (300 mL each). The combined organic extracts were dried with magnesium sulfate, filtered and evaporated. The desired product was obtained as an off-white solid (14.7 g, 85%) and used without any further purification for the next step.

Step 2: 2-Methyl-4-trimethylsilanylethynyl-pyridine

4-Iodo-2-methyl-pyridine (9.5 g, 41.8 mmol) was dissolved in 150 mL dry THF and 18 mL triethyl amine. This mixture was evacuated and backfilled with argon several times to remove oxygen from the solution. Triphenylphosphine (341 mg, 1.25 mmol) and bis(triphenylphosphine)palladium(II) chloride (1.47 g, 2.09 mmol) were added and the reaction mixture was stirred at RT for 1 h. Copper(I)iodide (248 mg, 1.3 mmol) and trimethylsilylacetylen (6.39 g, 6.50 mmol) were added. The reaction mixture was stirred at RT overnight. The solvent was evaporated. The residue was taken up in 500 mL water and extracted three times with ethyl acetate (500 mL each). The combined organic extracts were dried with magnesium sulfate, filtered and evaporated. The crude product was purified by flash chromatography on silica gel (heptane/ethyl acetate gradient 100:0→0:100). The desired product was obtained as a light brown liquid (8.18 g, 99%).

Step 3: 2-Methyl-4-(2-methyl-1H-imidazol-4-ylethynyl)-pyridine

Solution 1: 2-Methyl-4-trimethylsilanylethynyl-pyridine (12 g, 74 mmol) and 5-iodo-2-methyl-1H-imidazole (13.24 g, 64 mmol, synthesis: Cliff and Pyne, Synthesis 681–682 (1994) were dissolved in 75 mL dry THF and 20 mL dry DMF. This mixture was evacuated and backfilled with argon several times to remove oxygen from the solution.

Solution 2: Triphenylphosphine (223 mg, 0.85 mmol), bis (triphenylphosphine)-palladium(II)chloride (1.79 g, 2.55 mmol), copper(I)iodide (81 mg, 0.43 mmol) and triethyl amine (8.87 mL, 64 mmol) were dissolved in 75 mL dry THF. This mixture was also evacuated and backfilled with argon several times to remove oxygen from the solution.

Solution 2 was heated to 40° C. and solution 1 was added dropwise. The reaction mixture was heated to 60° C. and tetrabutylammonium fluoride solution (1M in THF, 55 mL, 55 mmol) was added dropwise during 45 min. The reaction was than stirred at RT overnight. The solvent was evaporated. The residue was taken up in 200 mL water and extracted three times with ethyl acetate (200 mL each). The combined organic extracts were dried with magnesium sulfate, filtered and evaporated. The crude product was purified by chromatography on silica gel (methylene chloride/methanol 95:5) and recrystallized from a mixture of methylene chloride and ethyl acetate. The desired product was obtained as a light brown solid (7.44 g, 59%).

4-(2-Isopropyl-1H-imidazol-4-ylethynyl)-2-methyl-pyridine (II-2) [MS: m/e=226.4 (M+H$^+$)] was prepared in analogy to the method as described in example II-1, method A2, step 3 from 2-methyl-4-trimethylsilanylethynyl-pyridine and 5-iodo-2-isopropyl-1H-imidazole.

EXAMPLE III-1

2-Chloro-5-methyl-pyrazine (III-1)

2-Hydroxy-5-methylpyrazine (0.984 g, 8.94 mmol) was refluxed in 15 mL phosphoroxychloride for 1.5 h. The reaction mixture was slowly poured into ice and adjusted to pH6 by addition of sodium carbonate. The mixture was extracted six times with ethyl acetate (50 mL each). The combined organic extracts were dried with sodium sulfate, filtered and evaporated. The crude product was used without any further purification for the next step.

EXAMPLE III-2

4-Chloro-2-trifluoromethyl-pyrimidine (III-2)

This compound was prepared according to Inoue et al., J. Org. Chem. 26:4504 (1961).

EXAMPLE III-3

2-Bromo-6-fluoro-pyridine (III-3)

This compound was prepared according to WO 92/11,241.

EXAMPLE IV-1

4-Ethynyl-1-(4-fluoro-phenyl)-2-methyl-1H-imidazole (IV-1)

Step 1: 1-(4-Fluoro-phenyl)-1H-imidazole-4-carboxylic acid ethyl ester

4-Fluoroaniline (20.0 g, 175 mmol) was mixed at RT with triethyl orthoformate (35.4 g, 233 mmol), ethylnitro acetate (28.5 g, 210 mmol) and 4 mL glacial acetic acid. The reaction mixture was refluxed with mechanical stirring for 2 h. More triethyl orthoformate (200 mL) and glacial acetic acid (200 mL) were added. Iron powder (100 g, 1.79 mol) was added in 3 portions during 8 h while maintaining the reaction mixture at reflux. Ethyl acetate (700 mL) was added and reflux was continued for another 2 h. The reaction mixture was filtered through a dicalite speed plus pad and washed with 500 mL ethyl acetate. The solvents were evaporated and the crude product was used without any further purification for the next step.

Step 2: 1-(4-Fluoro-phenyl)-1H-imidazole-4-carboxylic acid

Crude 1-(4-fluoro-phenyl)-1H-imidazole-4-carboxylic acid ethyl ester (175 mmol) was dissolved in 450 mL dioxane and 450 mL 2N sodium hydroxide solution. The reaction mixture was refluxed for 2 h. Charcoal (1 g, Norit SA II) was added and reflux was continued for another 20 min. The mixture was filtered hot and washed with 50 mL 2N sodium hydroxide solution. The filtrate was treated with 550 mL 2N HCl and stirred at RT overnight. The solid material was filtered off and dried at 50° C. and 15 mbar. The desired compound was obtained as an off-white solid (28 g, 78%), MS: m/e=205.1 (M–H).

Step 3: [1-(4-Fluoro-phenyl)-1H-imidazol-4-yl]-methanol 1-(4-Fluoro-phenyl)-1H-imidazole-4-carboxylic acid (18 g, 87 mmol) was dissolved in 90 mL dry THF. Borane tetrahydrofuran complex (174 mL, 1M in THF, 174 mmol) was added dropwise. The reaction was refluxed for 2 h and stirred at RT overnight. The reaction mixture was cooled to 0° C. and 100 mL methanol were added dropwise. The solvents were evaporated. The residue was taken up in 100 mL 2N HCl and refluxed for 2 h. The reaction mixture was then cooled to 0° C. and 120 mL 2N sodium hydroxide solution were added dropwise. The solid material was filtered off and dried at 50° C. and 15 mbar. The desired compound was obtained as a white solid (13 g, 78%), MS: m/e=193.2 (M+H)$^+$.

Step 4: 4-(tert-Butyl-dimethyl-silanyloxymethyl)-1-(4-fluoro-phenyl)-1H-imidazole

[1-(4-Fluoro-phenyl)-1H-imidazol-4-yl]-methanol (13 g, 67.5 mmol) was dissolved 65 mL DMF. Imidazole (11 g, 162 mmol) and tert. butyldimethyl chlorosilane (12.2 g, 81 mmol) were added. The reaction mixture was stirred at 45° C. overnight and poured into 500 mL water. The aqueous phase was extracted three times with ethyl acetate (200 mL each). The combined organic extracts were dried with magnesium sulfate, filtered and evaporated. The crude product was purified by column chromatography on silica gel (methylene chloride/methanol 98:2) and the desired compound was obtained as a light brown oil (20 g, 96%), MS: m/e=291.2 (M-CH$_3$), m/e=249.1 (M-tert. butyl).

Step 5: 4-(tert-Butyl-dimethyl-silanyloxymethyl)-1-(4-fluoro-phenyl)-2-methyl-1H-imidazole 4-(tert-Butyl-dimethyl-silanyloxymethyl)-1-(4-fluoro-phenyl)-1H-imidazole (18.2 g, 59.2 mmol) was dissolved in 600 mL dry THF and cooled to –78° C. n-Butyl lithium (55.5 mL, 1.6M in hexane, 88.8 mmol) was added dropwise. The reaction mixture was warmed up to –25° C., kept at –25° C. for 10 min and then cooled again to –78° C. Iodomethane (7.4 mL, 11.9 mmol) was added dropwise. The reaction mixture was slowly warmed up to RT and stirred at RT overnight. The solvent was evaporated. The residue was taken up in 300 mL water and extracted three times with ethyl acetate (200 mL each). The combined organic extracts were dried with magnesium sulfate, filtered and evaporated. The crude product was purified by column chromatography on silica gel (cyclohexane/ethyl acetate 50:50→20:80 gradient) and the desired compound was obtained as an orange oil (14.7 g, 77%), MS: m/e=321.1 (M+H$^+$).

Step 6: [1-(4-Fluoro-phenyl)-2-methyl-1H-imidazol-4-yl]-methanol 4-(tert-Butyl-dimethyl-silanyloxymethyl)-1-(4-fluoro-phenyl)-2-methyl-1H-imidazole (14.7 g, 45.7 mmol) was dissolved in 200 mL THF. Tetrabutyl ammoniumfluoride (91 mL, 1M in THF, 91 mmol) was added and the reaction mixture was stirred at RT overnight. The solvent was evaporated. The residue was taken up in 200 mL water and extracted three times with ethyl acetate (200 mL each). The combined organic extracts were dried with magnesium sulfate, filtered and evaporated. The crude product was suspended in 150 mL ethyl acetate, filtered and dried. The desired compound was obtained as a white solid (7.16 g, 76%), MS: m/e=207.1 (M+H$^+$).

Step 7: 1-(4-Fluoro-phenyl)-2-methyl-1H-imidazole-4-carbaldehyde

[1-(4-Fluoro-phenyl)-2-methyl-1H-imidazol-4-yl]-methanol (7.16 g, 34.7 mmol) was dissolved in 2.3 L methylene chloride. Mangan (IV) oxid (26.8 g, 278 mmol) was added and the reaction mixture was stirred at RT for 3 days. The suspension was filtered through a dicalite speed plus pad and washed with 1 L methylene chloride. The solvents were evaporated and the desired compound was obtained as a white solid (5.87 g, 83%), MS: m/e=205.1 (M+H$^+$).

Step 8: 4-Ethynyl-1-(4-fluoro-phenyl)-2-methyl-1H-imidazole (1-Diazo-2-oxo-propyl)-phosphonic acid dimethyl ester (6.51 g, 33.9 mmol) was dissolved in 100 mL methanol. Potassium carbonate (7.81 g, 56.5 mmol) was added. A solution of 1-(4-fluoro-phenyl)-2-methyl-1H-imidazole-4- carbaldehyde (5.77 g, 45 mmol) in 100 mmol methanol was added dropwise at RT. The reaction mixture was stirred at RT overnight. The solvent was evaporated. The residue was taken up in 150 mL water and extracted three times with ethyl acetate (150 mL each). The combined organic extracts were dried with sodium sulfate, filtered and evaporated. The crude product was purified by flash chromatography on silica gel (heptane/ethyl acetate 100:0→0:100 gradient) and the desired compound was obtained as a white solid (3.81 g, 67%), MS: m/e=200.1 (M+).

1-(3,4-Dichloro-phenyl)-4-ethynyl-2-methyl-1H-imidazole (IV-2) [MS: m/e=252.1 (M+)] was prepared in accordance with the method of example IV-1 from 3,4-dichloroaniline.

EXAMPLE V-1

2-Cyclopropyl-1-(4-fluoro-phenyl)-4-iodo-1H-imidazole (V-1)

Step 1: 2-Cyclopropyl-4,5-diiodo-1H-imidazole

2-Cyclopropyl-1H-imidazole (2500 mg, 23.12 mmol) was suspended in 46 ml 2N NaOH. A solution of iodine (11.74 g, 46.23 mmol) in 45 ml dichloromethane was added dropwise to the suspension within 15 min. The two-layer-mixture was stirred vigorously at RT over night. The aqueous layer was separated, neutralized with acetic acid and saturated $Na_2S_2O_3$-solution was added until the solution remained colorless. The suspension was stirred for 10 min, filtered and the solid was dried over night at 50° C. under reduced pressure (<10 mbar). The desired compound was obtained as a light brown solid (3.51 g, 42%).

Step 2: 2-Cyclopropyl-4-iodo-1H-imidazole $Na_2SO_3$ (10.42 g, 82.65 mmol) was suspended in 40 ml water and 20 ml ethanol. 2-Cyclopropyl-4,5-diiodo-1H-imidazole (3500 mg, 9.72 mmol) was added and the mixture was stirred at reflux for 16 hours. The reaction mixture was concentrated to 20 ml and then filtered. The solid was dried for 5 hours at 50° C. under reduced pressure (<10 mbar) to get a light brown solid (1.50 g, 66%), MS: m/e=235.1 (M+H+).

Step 3: 2-Cyclopropyl-1-(4-fluoro-phenyl)-4-iodo-1H-imidazole

2-Cyclopropyl-4-iodo-1H-imidazole (500 mg, 2.14 mmol) was dissolved in 20 ml THF. 4-Fluorobenzene boronic acid (613 mg, 4.38 mmol) and [Cu(OH)TMEDA]$_2$Cl$_2$ (347 mg, 0.75 mmol) were added. Oxygen was bubbled through the reaction mixture for 60 min and stirring was continued under an oxygen atmosphere at RT overnight. The reaction mixture was filtered through a dicalite speed plus pad and washed with 30 mL ethyl acetate. After drying the crude product was purified by flash chromatography on silica gel (heptane/ethyl acetate 90:10→50:50 gradient) to get the desired compound as a white solid (320 mg, 46%), MS: m/e=329.1 (M+H+).

Preparation of the Compounds of Formula I

EXAMPLE 1

4-[1-(4-Fluoro-phenyl)-2-methyl-1H-imidazol-4-ylethynyl]-2-methyl-pyridine (1)

Method A:

2-Methyl-4-(2-methyl-1H-imidazol-4-ylethynyl)-pyridine (II-1) (200 mg, 1.01 mmol) was dissolved in 10 mL dichloromethane. Powdered molecular sieves (3 Å, 200 mg), 4-fluorobenzene boronic acid (284 mg, 2.02 mmol) and [Cu(OH)TMEDA]$_2$Cl$_2$ (47 mg, 0.10 mmol) were added. Oxygen was bubbled through the reaction mixture for 5 min and stirring was continued at RT overnight. The reaction mixture was filtered through a dicalite speed plus pad and washed with 50 mL dichloromethane. The filtrate was washed with 50 ml water, dried with magnesium sulfate, filtered and evaporated. The crude product was purified by flash chromatography on silica gel (dichloromethane/methanol 100:0→85:15 gradient) and a mixture of 2 regioisomers was isolated. The desired compound was obtained by recrystallization from diethylether as a white solid (151 mg, 51%), mp=151° C., MS: m/e=292.1 (M+H+).

Method B:

4-Iodo-2-methyl-pyridine (656 mg, 3.0 mmol) was dissolved in 10 mL dry THF and 10 mL piperidine. This mixture was evacuated and backfilled with argon several times to remove oxygen from the solution. Triphenylphosphine (20 mg, 0.07 mmol) and bis(triphenylphosphin)palladium(II)chloride (175 mg, 0.10 mmol) were added and the reaction mixture was stirred at RT for 1 h. Copper(I)iodide (14 mg, 0.07 mmol) and 4-ethynyl-1-(4-fluoro-phenyl)-2-methyl-1H-imidazole (IV-1) (500 mg, 2.5 mmol) were added. The reaction mixture was then refluxed for 3 h. The solvent was evaporated. The residue was taken up in 30 mL water and extracted three times with ethyl acetate (50 mL each). The combined organic extracts were dried with magnesium sulfate, filtered and evaporated. The crude product was purified by flash chromatography on silica gel (dichloromethane/methanol 100:0→90:10 gradient) and recrystallization from diethylether and the desired product was obtained as a light yellow solid (250 mg, 34%), mp=151° C., MS: m/e=292.1 (M+H+).

4-[1-(3,4-Dichloro-phenyl)-2-methyl-1H-imidazol-4-ylethynyl]-2-methyl-pyridine hydrochloride (2) [MS: m/e=341.9 (M+H+)] was prepared in analogy to the method as described in Example 1 Method B starting from 1-(3,4-dichloro-phenyl)-4-ethynyl-2-methyl-1H-imidazole (IV-2) and 4-iodo-2-methyl-pyridine. For further purification the compound was precipitated as its HCl salt from an etheral solution.

Method C:

4-Iodo-2-methyl-1H-imidazole (200 mg, 1.0 mmol), 4-fluorophenylboronic acid (215 mg, 1.6 mmol), copper(II) acetate (210 mg, 1.2 mmol) and Et$_3$N (0.16 ml, 1.2 mmol) were suspended in 10 ml THF and oxygen was bubbled through the reaction mixture for 40 min. The reaction mixture was stirred for 48 hours at RT and then filtrated over dicalit. The filtrate was concentrated and then purified by flash chromatography to yield 1-(4-fluoro-phenyl)-4-iodo-2-methyl-1H-imidazole (120 mg, 0.40 mmol, 41%).

A solution of 1-(4-fluoro-phenyl)-4-iodo-2-methyl-1H-imidazole (5.0 g, 17mmol) and 2-methyl-4-trimethylsilanylethynyl-pyidine (3.2 g, 17 mmol, prepared from 4-iodo-2-methyl pyridine and commercially available ethynyl-trimethyl-silane in a Sonogashira reaction) in 15 ml THF was transferred to a mixture of triphenylphosphine (88 mg, 0.34 mmol), bis(tri-phenylphosphin)palladium(II)chloride (705 mg, 1.0 mmol) and Et$_3$N (3.5 ml. 25 mmol) in 80 ml THF. Copper(I)iodide (32 mg, 0.17 mmol) was added and the reaction mixture was heated under argon atmosphere to 40° C. and a solution of tetrabutylammoniumfluoride (1 M in THF, 25.1 ml) was added over a period of 40 min. The reaction mixture was stirred for three hours at 40° C. and then for 48 hours at RT. After aqueous work up and purification by chromatography over silica gel and crystallization from ethylacetate and hexane the desired product was obtained as a light yellow solid (2.8 g, 57%, mp=151° C., MS: m/e=292.1 (M+H+)).

The following compounds were prepared in analogy to the method as described in the above Method A:

| Compound name and number | Compound of formula III | MS: m/e mp |
|---|---|---|
| 4-[1-(2,4-difluoro-phenyl)-2-methyl-1H-imidazol-4-ylethynyl]-2-methyl-pyridine (3) | 2,4-difluorophenyl boronic acid | 310.1 (M + H⁺) 156–157° C. |
| 4-[1-(3,4-difluoro-phenyl)-2-methyl-1H-imidazol-4-ylethynyl]-2-methyl-pyridine (4) | 3,4-difluorophenyl boronic acid | 309.1 (M⁺) 163–164° C. |
| 4-[2-methyl-4-(2-methyl-pyridin-4-ylethynyl)-imidazol-1-yl]-benzonitrile (5) | 4-cyanophenyl boronic acid | 299.2 (M + H⁺) 186–187° C. |
| 3-[2-methyl-4-(2-methyl-pyridin-4-ylethynyl)-imidazol-1-yl]-benzonitrile (6) | 3-cyanophenyl boronic acid | 299.2 (M + H⁺) 173–174° C. |
| 2-methyl-4-[2-methyl-1-(3-trifluoromethyl-phenyl)-1H-imidazol-4-ylethynyl]-pyridine (7) | 3-trifluoromethyl-phenyl boronic acid | 341.1 (M⁺) 131–132° C. |
| 4-[1-(4-chloro-phenyl)-2-methyl-1H-imidazol-4-ylethynyl]-2-methyl-pyridine (9) | 4-chloro-phenyl boronic acid | 308.3 (M + H⁺) |
| 4-[1-(3-fluoro-phenyl)-2-methyl-1H-imidazol-4-ylethynyl]-2-methyl-pyridine (10) | 3-fluoro-phenyl boronic acid | 291.9 (M + H⁺) |
| 4-[1-(3,5-difluoro-phenyl)-2-methyl-1H-imidazol-4-ylethynyl]-2-methyl-pyridine (11) | 3,5-difluoro-phenyl boronic acid | 310.1 (M + H⁺) |
| 4-[1-(3-fluoro-4-methyl-phenyl)-2-methyl-1H-imidazol-4-ylethynyl]-2-methyl-pyridine (12) | 3-fluoro-4-methyl-phenyl boronic acid | 306.2 (M + H⁺) |
| 4-[1-(3-chloro-4-fluoro-phenyl)-2-methyl-1H-imidazol-4-ylethynyl]-2-methyl-pyridine (13) | 3-chloro-4-fluoro-phenyl boronic acid* | 326.3 (M + H⁺) |
| 2-methyl-4-(2-methyl-1-p-tolyl-1H-imidazol-4-ylethynyl)-pyridine (14) | 4-methyl-phenyl boronic acid | 288.1 (M + H⁺) |
| 4-[1-(4-methoxy-phenyl)-2-methyl-1H-imidazol-4-ylethynyl]-2-methyl-pyridine (15) | 4-methoxy-phenyl boronic acid | 304.1 (M + H⁺) |
| 2-methyl-4-[2-methyl-1-(4-trifluoromethyl-phenyl)-1H-imidazol-4-ylethynyl]-pyridine (16) | 4-trifluoromethyl-phenyl boronic acid | 342.0 (M + H⁺) |
| 2-methyl-4-[2-methyl-1-(3-trifluoromethoxy-phenyl)-1H-imidazol-4-ylethynyl]-pyridine (17) | 3-trifluoromethoxy-phenyl boronic acid | 358.0 (M + H⁺) |
| 1-methyl-5-[2-methyl-4-(2-methyl-pyridin-4-ylethynyl)-imidazol-1-yl]-1H-indole (18) | N-methylindole-5-boronic acid | 327.1 (M + H⁺) |

*recrystallization of the resulting regioisomers-mixture in ethyl acetate at RT

EXAMPLE 2

2-[2-Methyl-4-(2-methyl-pyridin-4-ylethynyl)-imidazol-1-yl]-pyrimidine (8)

2-Methyl-4-(2-methyl-1H-imidazol-4-ylethynyl)-pyridine (II-1) (87 mg, 0.44 mmol) dissolved in 3 mL dimethyl formamide. Potassium carbonate (122 mg, 0.88 mmol) and 2-chloro-pyrimidine (76 mg, 0.66 mmol) were added and the reaction mixture was refluxed overnight. The reaction mixture was poured into 60 mL water and extracted three times with ethyl acetate (50 mL each). The combined organic extracts were dried with sodium sulfate, filtered and evaporated. The crude product was treated with ethyl acetate (2 mL) and diisopropyl ether (2 mL). The solid was filtered off and washed with little diisoppropyl ether. The desired compound was as an off-white solid (49 mg, 50%), mp=164–165° C., MS: m/e=276.1 (M+H⁺).

The following compounds were prepared in analogy to the method as described above:

| Compound name and number | Starting compounds | MS: m/e mp |
|---|---|---|
| 4,6-dimethyl-2-[2-methyl-4-(2-methyl-pyridin-4-ylethynyl)-imidazol-1-yl]-pyrimidine (19) | (II-1) and 2-chloro-4,6-dimethyl-pyrimidine | 304.2 (M + H⁺) |
| 4-methyl-2-[2-methyl-4-(2-methyl-pyridin-4-ylethynyl)-imidazol-1-yl]-pyrimidine (20) | (II-1) and 2-chloro-4-methyl-pyrimidine | 290.1 (M + H⁺) |
| 2-[2-methyl-4-(2-methyl-pyridin-4-ylethynyl)-imidazol-1-yl]-4-trifluoromethyl-pyrimidine (21) | (II-1) and 2-chloro-4-(trifluoromethyl)-pyrimidine | 344.1 (M + H⁺) |
| 4-methoxy-2-[2-methyl-4-(2-methyl-pyridin-4-ylethynyl)-imidazol-1-yl]-pyrimidine (22) | (II-1) and 2-chloro-4-methoxy-pyrimidine | 306.4 (M + H⁺) |
| 5-ethyl-2-[2-methyl-4-(2-methyl-pyridin-4-ylethynyl)-imidazol-1-yl]-pyrimidine (23) | (II-1) and 2-chloro-5-ethyl-pyrimidine | 304.2 (M + H⁺) |
| 5-fluoro-2-[2-methyl-4-(2-methyl-pyridin-4-ylethynyl)-imidazol-1-yl]-pyrimidine (24) | (II-1) and 2-chloro-5-fluoro-pyrimidine* | 294.1 (M + H⁺) |
| 2-[2-methyl-4-(2-methyl-pyridin-4-ylethynyl)-imidazol-1-yl]-pyrazine (25) | (II-1) and 2-chloro-pyrazine | 276.0 (M + H⁺) |
| 2-methyl-5-[2-methyl-4-(2-methyl-pyridin-4-ylethynyl)-imidazol-1-yl]-pyrazine (26) | (II-1) and 2-chloro-5-methyl-pyrazine | 290.3 (M + H⁺) |
| 2-chloro-6-[2-methyl-4-(2-methyl-pyridin-4-ylethynyl)-imidazol-1-yl]-pyrazine (27) | (II-1) and 2,6-dichloro-pyrazine | 310.1 (M + H⁺) |
| 2-chloro-4-[2-methyl-4-(2-methyl-pyridin-4-ylethynyl)-imidazol-1-yl]-pyrimidine (28)** | (II-1) and 2,4-dichloro-pyrimidine | 310.0, 312.1 (M + H⁺) |

-continued

| Compound name and number | Starting compounds | MS: m/e mp |
|---|---|---|
| 4-chloro-2-[2-methyl-4-(2-methyl-pyridin-4-ylethynyl)-imidazol-1-yl]-pyrimidine (29)*** | (II-1) and 2,4-dichloro-pyrimidine | 310.0, 312.1 (M + H$^+$) |
| 4-[2-methyl-4-(2-methyl-pyridin-4-ylethynyl)-imidazol-1-yl]-2-methylsulfanyl-pyrimidine (30) | (II-1) and 4-chloro-2-methylthio-pyrimidine | 322.4 (M + H$^+$) |
| 4-[2-methyl-4-(2-methyl-pyridin-4-ylethynyl)-imidazol-1-yl]-2-trifluoromethyl-pyrimidine (31) | (II-1) and 4-chloro-2-trifluoromethyl-pyrimidine | 343.9 (M + H$^+$) |
| 2-[2-methyl-4-(2-methyl-pyridin-4-ylethynyl)-imidazol-1-yl]-pyridine (32) | (II-1) and 2-fluoro-pyridine | 275.0 (M + H$^+$) |
| 6-fluoro-2-[2-methyl-4-(2-methyl-pyridin-4-ylethynyl)-imidazol-1-yl]-pyridine (33) | (II-1) and 2,6-difluoro-pyridine | 293.4 (M + H$^+$) |
| 2-[2-methyl-4-(2-methyl-pyridin-4-ylethynyl)-imidazol-1-yl]-6-methylpyridine (34) | (II-1) and 2-fluoro-6-methyl-pyridine | 289.1 (M + H$^+$) |
| 2-[2-isopropyl-4-(2-methyl-pyridin-4-ylethynyl)-imidazol-1-yl]-6-methylpyridine (35) | (II-2) and 2-fluoro-6-methyl-pyridine | 317.4 (M + H$^+$) |
| 2-[2-methyl-4-(2-methyl-pyridin-4-ylethynyl)-imidazol-1-yl]-6-methyl-4-trifluoromethyl-pyridine (36) | (II-1) and 2-chloro-6-methyl-4-trifluoromethyl-pyridine | 357.4 (M + H$^+$) |
| 2-[2-methyl-4-(2-methyl-pyridin-4-ylethynyl)-imidazol-1-yl]-6-trifluoromethyl-pyridine (37) | (II-1) and 2-fluoro-6-trifluoromethyl-pyridine | 343.1 (M + H$^+$) |
| 2-[2-isopropyl-4-(2-methyl-pyridin-4-ylethynyl)-imidazol-1-yl]-6-trifluoromethyl-pyridine (38) | (II-2) and 2-fluoro-6-trifluoromethyl-pyridine | 371.1 (M + H$^+$) |
| 2-[2-methyl-4-(2-methyl-pyridin-4-ylethynyl)-imidazol-1-yl]-5-methyl-pyridine (39) | (II-1) and 2-fluoro-5-methyl-pyridine | 289.1 (M + H$^+$) |
| 2-[2-isopropyl-4-(2-methyl-pyridin-4-ylethynyl)-imidazol-1-yl]-5-methyl-pyridine (40) | (II-2) and 2-fluoro-5-methyl-pyridine | 317.2 (M + H$^+$) |
| 5-chloro-2-[2-methyl-4-(2-methyl-pyridin-4-ylethynyl)-imidazol-1-yl]-pyridine (41) | (II-1) and 2,5-dichloro-pyridine | 309.2 (M + H$^+$) |
| 5-bromo-2-[2-methyl-4-(2-methyl-pyridin-4-ylethynyl)-imidazol-1-yl]-pyridine (42) | (II-1) and 5-bromo-2-fluoro-pyridine | 352.8 (M + H$^+$) |
| 4-iodo-2-[2-methyl-4-(2-methyl-pyridin-4-ylethynyl)-imidazol-1-yl]-pyridine (43) | (II-1) and 2-fluoro-4-iodo-pyridine | 401.0 (M + H$^+$) |
| 2-[2-methyl-4-(2-methyl-pyridin-4-ylethynyl)-imidazol-1-yl]-4-methyl-pyridine (44) | (II-1) and 2-fluoro-4-methyl-pyridine | 289.1 (M + H$^+$) |
| 2-[2-methyl-4-(2-methyl-pyridin-4-ylethynyl)-imidazol-1-yl]-4-trifluoromethyl-pyridine (45) | (II-1) and 2-chloro-4-trifluoromethyl-pyridine | 343.2 (M + H$^+$) |
| 2-chloro-5-[2-methyl-4-(2-methyl-pyridin-4-ylethynyl)-imidazol-1-yl]-pyridine (46) | (II-1) and 2-chloro-5-fluoro-pyridine | 309.2 (M + H$^+$) |
| 2-bromo-5-[2-methyl-4-(2-methyl-pyridin-4-ylethynyl)-imidazol-1-yl]-pyridine (47) | (II-1) and 2-bromo-5-fluoro-pyridine | 353.1 (M + H$^+$) |
| 3-fluoro-5-[2-methyl-4-(2-methyl-pyridin-4-ylethynyl)-imidazol-1-yl]-pyridine (48) | (II-1) and 3,5-difluoro-pyridine | 293.1 (M + H$^+$) |
| 3-chloro-5-[2-methyl-4-(2-methyl-pyridin-4-ylethynyl)-imidazol-1-yl]-pyridine (49) | (II-1) and 3,5-dichloro-pyridine | 309.3 (M + H$^+$) |
| 4-fluoro-6-[2-methyl-4-(2-methyl-pyridin-4-ylethynyl)-imidazol-1-yl]-pyrimidine (50) | (II-1) and 4,6-difluoro-pyrimidine | 294.3 (M + H$^+$) |
| 5-bromo-2-[2-methyl-4-(2-methyl-pyridin-4-ylethynyl)-imidazol-1-yl]-pyrimidine (51) | (II-1) and 5-bromo-2-chloro-pyrimidine | 354.0 (M + H$^+$) |
| 2-bromo-6-[2-methyl-4-(2-methyl-pyridin-4-ylethynyl)-imidazol-1-yl]-pyridine (52) and 2-fluoro-6-[2-methyl-4-(2-methyl-pyridin-4-ylethynyl)-imidazol-1-yl]-pyridine (53) | (II-1) and 2-bromo-6-fluoro-pyridine | 293.3, 353.1 (M + H$^+$) |

*prepared according to Dunaiskis et al., Organic Preparations and Procedures International 2: 600–602 (1995)
**obtained as a mixture with 4-chloro-2-[2-methyl-4-(2-methyl-pyridin-4-ylethynyl)-imidazol-1-yl]-pyrimidine and could be separated by chromatography
***obtained as a mixture with 2-chloro-4-[2-methyl-4-(2-methyl-pyridin-4-ylethynyl)-imidazol-1-yl]-pyrimidine and could be separated by chromatography

EXAMPLE 3

4-[2-Cyclopropyl-1-(4-fluoro-phenyl)-1H-imidazol-4-yl-ethynyl]-2-methyl-pyridine (54)

2-Cyclopropyl-1-(4-fluoro-phenyl)-4-iodo-1H-imidazole (V-1) (150 mg, 0.46 mmol) and 2-methyl-4-trimethylsilanylethynyl-pyridine (113 mg, 0.59 mmol) were dissolved in 4 mL dry THF. This mixture was evacuated and backfilled with argon several times to remove oxygen from the solution. In a second reaction vessel triphenylphosphine (4 mg, 0.01 mmol), bis(triphenylphosphine)-palladium(II)chloride (16 mg, 0.02 mmol), copper(I)iodide (1 mg, 0.01 mmol) and triethyl amine (0.10 mL, 0.69 mmol) were dissolved in 2 mL dry THF. This mixture was also evacuated and backfilled with argon several times to remove oxygen from the solution. This mixture was heated to 40° C. and the solution of 2-cyclopropyl-1-(4-fluoro-phenyl)-4-iodo-1H-imidazole and 2-methyl-4-trimethylsilanylethynyl-pyridine was added dropwise. The reaction mixture was heated to 60° C. and tetrabutylammonium fluoride solution (1M in THF, 0.72 mL, 0.69 mmol) was added dropwise during 5 min. The reaction was than stirred at 40° C. for 2 hours. The mixture was taken up in 20 mL water and extracted three times with ethyl acetate (20 mL each). The combined organic extracts were dried with magnesium sulfate, filtered and evaporated. The crude product was purified by chromatography on silica gel (n-heptane/ethyl acetate 1:4) to obtain the desired title compound as a colorless solid (85 mg, 59%), MS: m/e=318.1 (M+H+).

EXAMPLE 4

2-Methyl-6-[2-methyl-4-(2-methyl-pyridin-4-ylethynyl)-imidazol-1-yl]-pyrazine (55), starting from a compound of formula I 2-Chloro-6-[2-methyl-4-(2-methyl-pyridin-4-ylethynyl)-imidazol-1-yl]-pyrazine (27)(300 mg, 0.968 mmol) was dissolved in 5 mL dry tetrahydrofuran. Dimethylzinc (1.2 mL, 2M in toluene) and tetrakis(triphenylphosphin)palladium (23 mg, 0.02 mmol) were added. The reaction mixture was refluxed for 2 h and poured into 50 mL sat. sodium bicarbonate solution. The mixture was extracted three times with ethyl acetate (50 mL each). The combined organic extracts were dried with magnesium sulfate, filtered and evaporated. The crude product was purified by flash chromatography on silica gel (dichloromethane/methanol 100:0→90:10 gradient) and the desired product was obtained as a light yellow solid (240 mg, 85%), MS: m/e=290.1 (M+H+).

The following compounds were prepared in analogy to the method as described above:

EXAMPLE 5

2-Butyl-6-[2-methyl-4-(2-methyl-pyridin-4-ylethynyl)-imidazol-1-yl]-pyridine (65)

The title compound, MS: m/e=331.3 (M+H+) was obtained as a by-product in the synthesis of 2-cyclopropyl-6-[2-methyl-4-(2-methyl-pyridin-4-ylethynyl)-imidazol-1-yl]-pyridine (57) due to n-butyllithium impurities in the cyclopropylzinc chloride solution.

EXAMPLE 6

2-Butyl-5-[2-methyl-4-(2-methyl-pyridin-4-ylethynyl)-imidazol-1-yl]-pyridine (66)

The title compound, MS: m/e=331.1 (M+H+) was obtained as a by-product in the synthesis of 2-cyclopropyl-5-[2-methyl-4-(2-methyl-pyridin-4-ylethynyl)-imidazol-1-yl]-pyridine (59) due to n-butyllithium impurities in the cyclopropylzinc chloride solution.

EXAMPLE 7

2-Methoxy-6-[2-methyl-4-(2-methyl-pyridin-4-ylethynyl)-imidazol-1-yl]-pyrazine (67)

The title compound, MS: m/e=306.5 (M+H+) was prepared by treatment of 100 mg 0.32 mmol) 2-chloro-6-[2-methyl-4-(2-methyl-pyridin-4-ylethynyl)-imidazol-1-yl]-pyrazine (27) with 5 equiv. of sodium methoxide in 4 ml of methanol (3 h, 55° C.). The compound, after extraction with ethyl acetate/water, was purified by chromatography. Yield: 62 mg (0.203 mmol, 63%).

| Compound name and number | Starting compounds | MS: m/e mp |
|---|---|---|
| 2-cyclopropyl-6-[2-methyl-4-(2-methyl-pyridin-4-ylethynyl)-imidazol-1-yl]-pyrazine (56) | (27) and cyclopropylzinc chloride* | 316.0 (M + H+) |
| 2-cyclopropyl-6-[2-methyl-4-(2-methyl-pyridin-4-ylethynyl)-imidazol-1-yl]-pyridine (57) | (52) and (53) and cyclopropylzinc chloride* | 315.3 (M + H+) |
| 5-[2-methyl-4-(2-methyl-pyridin-4-ylethynyl)-imidazol-1-yl]-2-methyl-pyridine (58) | (47) and dimethylzinc | 289.1 (M + H+) |
| 2-cyclopropyl-5-[2-methyl-4-(2-methyl-pyridin-4-ylethynyl)-imidazol-1-yl]-pyridine (59) | (47) and cyclopropylzinc chloride* | 315.0 (M + H+) |
| 4-cyclopropyl-2-[2-methyl-4-(2-methyl-pyridin-4-ylethynyl)-imidazol-1-yl]-pyridine (60) | (43) and cyclopropylzinc chloride* | 315.1 (M + H+) |
| 5-cyclopropyl-2-[2-methyl-4-(2-methyl-pyridin-4-ylethynyl)-imidazol-1-yl]-pyridine (61) | (42) and cyclopropylzinc chloride* | 315.1 (M + H+) |
| 5-methyl-2-[2-methyl-4-(2-methyl-pyridin-4-ylethynyl)-imidazol-1-yl]-pyrimidine (62) | (42) and dimethylzinc | 290.0 (M + H+) |
| 2-cyclopropyl-4-[2-methyl-4-(2-methyl-pyridin-4-ylethynyl)-imidazol-1-yl]-pyrimidine (63) | (28) and cyclopropylzinc chloride* | 316.0 (M + H+) |
| 4-cyclopropyl-2-[2-methyl-4-(2-methyl-pyridin-4-ylethynyl)-imidazol-1-yl]-pyrimidine (64) | (29) and cyclopropylzinc chloride* | 316.1 (M + H+) |

*prepared according to De Lang and Brandsma, Synthetic Communications 28: 225–232 (1998)

2-Methoxy-6-[2-methyl-4-(2-methyl-pyridin-4-ylethynyl)-imidazol-1-yl]-pyridine (68) [MS: m/e=305.4 (M+H⁺)] was prepared in analogy to the method as described above from 6-fluoro-2-[2-methyl-4-(2-methyl-pyridin-4-ylethynyl)-imidazol-1-yl]-pyridine (33).

EXAMPLE 8

2-Methoxy-4-[2-methyl-4-(2-methyl-pyridin-4-yl-ethynyl)-imidazol-1-yl]-pyridine (69)

Following the Buchwald-protocol [Buchwald et al., Tetrahedron Lett. 40:2657 (1999)], a rigorously dried Schlenk tube was filled with argon and charged with copper(I) trifluoromethanesulfonate benzene complex (101 mg, 0.2 mmol), phenanthroline (720 mg, 4.0 mmol), dibenzylideneacetone (47 mg, 0.2 mmol) and cesium carbonate (2.86 g, 8.8 mmol). 2-Methyl-4-(2-methyl-1H-imidazol-4-ylethynyl)-pyridine (II-1) (1.18 g, 6.0 mmol), o-xylene (1.6 ml) and 4-iodo-2-methoxypyridine x HCl (1.1 g, 4.0 mmol) [Talik and Plazek, Rocz. Chem. 33:1343 (1959)] was added. The mixture was stirred at 110° C. for 24 hr, cooled to RT and partitioned between CH$_2$Cl$_2$ and saturated aqueous NH$_4$Cl solution. The organic phase was concentrated and purified by chromatography on silica gel (dichloromethane/methanol 100:0→97:3 gradient). The title compound was obtained as a tan semisolid material (44 mg, 4%). The free base was converted to the HCL salt. mp=145–147° C. (MeOH/Et$_2$O), MS: m/e=305.0 (M+H⁺).

EXAMPLE 9

Dimethyl-{5-[2-methyl-4-(2-methyl-pyridin-4-yl-ethynyl)-imidazol-1-yl]-pyridin-3-yl}-amine (70)

3-Fluoro-5-[2-methyl-4-(2-methyl-pyridin-4-ylethynyl)-imidazol-1-yl]-pyridine (48) (100 mg, 0.34 mmol) was dissolved in 5 mL dimethyl formamide. Potassium carbonate (189 mg, 1.38 mmol) and dimethylamine hydrochloride (42 mg, 0.52 mmol) were added and the reaction mixture was refluxed overnight. The reaction mixture was poured into 60 mL water and extracted three times with ethyl acetate (50 mL each). The combined organic extracts were dried with sodium sulfate, filtered and evaporated. The crude product was purified by flash chromatography on silica gel (dichloromethane/methanol 100:0→90:10 gradient) and the desired compound was obtained as an off-white solid (22 mg, 20%), MS: m/e=318.2 (M+H⁺).

The following compounds were prepared in analogy to the method as described above:

| Compound name and number | Starting compounds | MS: m/e mp |
|---|---|---|
| dimethyl-{6-[2-methyl-4-(2-methyl-pyridin-4-ylethynyl)-imidazol-1-yl]-pyridin-2-yl}-amine (71) | (33) and dimethylamine hydrochloride | 318.4 (M + H⁺) |
| dimethyl-{6-[2-methyl-4-(2-methyl-pyridin-4-ylethynyl)-imidazol-1-yl]-pyrazin-2-yl}-amine (72) | (27) and dimethylamine hydrochloride | 319.4 (M + H⁺) |
| ethyl-{5-[2-methyl-4-(2-methyl-pyridin-4-ylethynyl)-imidazol-1-yl]-pyridin-3-yl}-amine (73) | (48) and ethylamine hydrochloride | 317.2 (M⁺) |
| methyl-{6-[2-methyl-4-(2-methyl-pyridin-4-ylethynyl)-imidazol-1-yl]-pyridin-2-yl}-amine (74) | (33) and methylamine hydrochloride | 304.4 (M + H⁺) |
| methyl-{6-[2-methyl-4-(2-methyl-pyridin-4-ylethynyl)-imidazol-1-yl]-pyrazin-2-yl}-amine (75) | (27) and methylamine hydrochloride | 305.0 (M + H⁺) |
| Cyclopropyl-{6-[2-methyl-4-(2-methyl-pyridin-4-ylethynyl)-imidazol-1-yl]-pyrazin-2-yl}-amine (76) | (27) and cyclopropylamine | 331.3 (M + H⁺) |
| 1-{5-[2-methyl-4-(2-methyl-pyridin-4-ylethynyl)-imidazol-1-yl]-pyridin-3-yl}-pyrrolidine (77) | (48) and pyrrolidine | 344.2 (M + H⁺) |
| 1-{6-[2-methyl-4-(2-methyl-pyridin-4-ylethynyl)-imidazol-1-yl]-pyridin-2-yl}-pyrrolidine (78) | (33) and pyrrolidine | 344.3 (M + H⁺) |
| 1-{3-[2-Methyl-4-(2-methyl-pyridin-4-ylethynyl)-imidazol-1-yl]-pyridin-5-yl}-piperidine (79) | (48) and piperidine | 358.2 (M + H⁺) |
| 4-{6-[2-Methyl-4-(2-methyl-pyridin-4-ylethynyl)-imidazol-1-yl]-pyridin-2-yl}-morpholine (80) | (33) and morpholine | 360.5 (M + H⁺) |
| 4-{6-[2-Methyl-4-(2-methyl-pyridin-4-ylethynyl)-imidazol-1-yl]-pyrazin-2-yl}-morpholine (81) | (27) and morpholine | 361.5 (M + H⁺) |
| 4-{6-[2-Methyl-4-(2-methyl-pyridin-4-ylethynyl)-imidazol-1-yl]-pyridin-2-yl}-thiomorpholine (82) | (33) and thiomorpholine | 376.4 (M + H⁺) |
| (2-Methoxy-ethyl)-methyl-{6-[2-methyl-4-(2-methyl-pyridin-4-ylethynyl)-imidazol-1-yl]-pyridin-2-yl}-amine (83) | (33) and 2-(methoxy-ethyl)-methyl-amine | 362.3 (M + H⁺) |

-continued

| Compound name and number | Starting compounds | MS: m/e mp |
|---|---|---|
| (2-Methoxy-ethyl)-{6-[2-methyl-4-(2-methyl-pyridin-4-ylethynyl)-imidazol-1-yl]-pyridin-2-yl}-amine (84) | (33) and 2-(methoxy-ethyl)-amine | 348.4 (M + H$^+$) |
| Benzyl-{5-[2-methyl-4-(2-methyl-pyridin-4-ylethynyl)-imidazol-1-yl]-pyridin-3-yl}-amine (85) | (48) and benzyl amine | 380.4 (M$^+$) |

EXAMPLE 10

2-(2-Methoxy-ethoxy)-6-[2-methyl-4-(2-methyl-pyridin-4-ylethynyl)-imidazol-1-yl]-pyrazine (86)

The title compound, MS: m/e=350.4 (M+H$^+$) was prepared by treatment of 100 mg 0.32 mmol) 2-chloro-6-[2-methyl-4-(2-methyl-pyridin-4-ylethynyl)-imidazol-1-yl]-pyrazine (27) with 3 equiv. of 2-methoxyethanol and 3 equiv. of sodium hydride in 5 ml of THF (1 h, 50° C.). The compound, after extraction with methylene chloride/water, was purified by chromatography. Yield: 45 mg (0.13 mmol, 40%).

2-(2-Methoxy-ethoxy)-6-[2-methyl-4-(2-methyl-pyridin-4-ylethynyl)-imidazol-1-yl]-pyridine (87) [MS: m/e=349.3 (M+H$^+$)] was prepared in analogy to the method as described above from 6-fluoro-2-[2-methyl-4-(2-methyl-pyridin-4-ylethynyl)-imidazol-1-yl]-pyridine (33).

EXAMPLE 11

4-[1-(4-Fluoro-phenyl)-2,5-dimethyl-1H-imidazol-4-ylethynyl]-2-methyl-pyridine (88)

Diisopropylamine (0.260 mg, 2.6 mmol) was dissolved in 5 mL dry tetrahydrofurane, n-butyllithium (1.6 mL, 1.6 M in hexane, 2.6 mmol) were added at −78° C. and the mixture was kept at −78° C. for 10 min. 4-[1-(4-Fluoro-phenyl)-2-methyl-1H-imidazol-4-ylethynyl]-2-methyl-pyridine (1) (500 mg, 1.72 mmol) in 5 mL dry tetrahydrofurane was added at −78° C. and stirring was continued for 45 min at this temperature. Methyl iodide (410 mg, 2.9 mmol) was added at −78° C. and the reaction mixture was slowly warmed to RT. The reaction mixture was quenched by addition of 50 mL water and extracted three times with diethylether (100 mL each). The combined organic extracts were dried with sodium sulfate, filtered and evaporated. The crude product was purified by column chromatography on silica gel (methylenchloride/methanol 9:1) and the desired compound was obtained as a white solid (325 mg, 62%), MS: m/e=306.4 (M+H$^+$).

3-(4-Fluoro-phenyl)-2-methyl-5-(2-methyl-pyridin-4-ylethynyl)-3H-imidazole-4-carbaldehyde (89) [MS: m/e=320.4 (M$^+$)] was prepared in analogy to the method as above from 4-[1-(4-Fluoro-phenyl)-2-methyl-1H-imidazol-4-ylethynyl]-2-methyl-pyridine (1) and N,N-dimethyl-formamide.

Preparation of the Pharmaceutical Compositions:

EXAMPLE I

Tablets

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE II

Tablets

Tablets of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE III

Capsules

Capsules of the following composition are produced:

|  | mg/Capsule |
|---|---|
| Active ingredient | 50 |
| Crystalline. lactose | 60 |
| Microcrystalline cellulose | 34 |

-continued

|  | mg/Capsule |
|---|---|
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula I

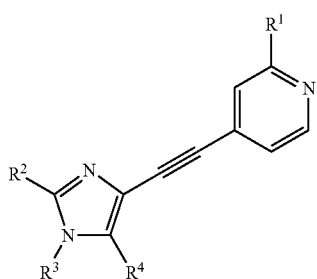

(I)

wherein
R$^1$ is C$_1$–C$_6$alkyl;
R$^2$ is C$_1$–C$_6$alkyl or C$_3$–C$_{12}$cycloalkyl;
R$^3$ is aryl that is unsubstituted or substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_1$–C$_6$alkylamino, di-C$_1$–C$_6$alkylamino, C$_1$–C$_6$alkoxyamino, (C$_1$–C$_6$alkoxy)C$_1$–C$_6$alkylamino, C$_3$–C$_{12}$cycloalkylamino, benzylamino and cyano; and
R$^4$ is hydrogen, C(O)H or CH$_2$R$^5$ wherein R$^5$ is hydrogen, OH, C$_1$–C$_6$alkyl or C$_3$–C$_{12}$cycloalkyl
or a pharmaceutically acceptable salt thereof.

2. The compound of formula I according to claim 1 wherein R$^1$ is methyl.

3. The compound of formula I according to claim 1 wherein R$^2$ is C$_1$–C$_6$alkyl.

4. The compound of formula I according to claim 3 wherein R$^2$ is methyl or isopropyl.

5. The compound of formula I according to claim 1 wherein R$^2$ is cycloalkyl.

6. The compound of formula I according to claim 5 wherein R$^2$ is cyclopropyl.

7. The compound of formula I according to claim 1 wherein R$^3$ is unsubstituted aryl or aryl substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_1$–C$_6$alkylamino, di-C$_1$–C$_6$alkylamino, C$_1$–C$_6$alkoxyamino, (C$_1$–C$_6$alkoxy)C$_1$–C$_6$alkylamino, C$_3$–C$_{12}$cycloalkylamino, and cyano.

8. The compound of formula I according to claim 1 wherein R$^3$ is aryl or aryl substituted by benzylamino.

9. The compound of formula I according to claim 1 wherein R$^4$ is hydrogen, C(O)H or CH$_3$.

10. The compound of formula I according to claim 1 wherein R$^3$ is unsubstituted phenyl or phenyl substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_1$–C$_6$alkylamino, di-C$_1$–C$_6$alkylamino, C$_1$–C$_6$alkoxyamino, (C$_1$–C$_6$alkoxy)C$_1$–C$_6$alkylamino, C$_3$–C$_{12}$cycloalkylamino, benzylamino and cyano.

11. The compound of formula I according to claim 10 wherein R$^3$ is unsubstituted phenyl or phenyl substituted by one or two substituents selected from halogen, C$_1$–C$_6$alkyl, C$_1$–C$_6$alkyl-halogen, C$_1$–C$_6$alkoxy, halogen-C$_1$–C$_6$alkoxy, and cyano.

12. The compound of formula I according to claim 11 wherein R$^3$ is unsubstituted phenyl or phenyl substituted by one or two substituents selected from fluoro, chloro, methyl, trifluoromethyl, methoxy, trifluoromethoxy, and cyano.

13. The compound of formula I according to claim 10 wherein R$^3$ is fluorophenyl, difluorophenyl, chlorophenyl, dichlorophenyl, cyanophenyl, trifluoromethylphenyl, fluoro-methylphenyl, chloro-fluorophenyl, methylphenyl, methoxyphenyl or trifluoromethoxyphenyl.

14. The compound according to claim 1 having the formula I*

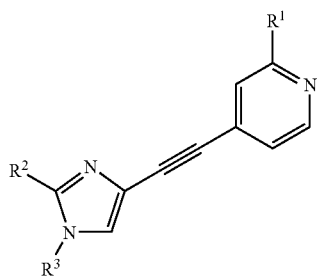

(I*)

wherein
R$^1$ signifies lower alkyl;
R$^2$ signifies lower alkyl;
R$^3$ signifies aryl optionally substituted, by one, two or three substituents, selected from the group consisting of halogen, lower alkyl, lower alkyl-halogen or cyano.

15. The compound according to claim 14 where R$^1$ and R$^2$ are both methyl.

16. The compound according to claim 14 wherein R$^3$ is substituted phenyl.

17. The compound according to claim 16 wherein the substitution is selected from fluoro, chloro, cyano, and trifluoromethyl.

18. The compound according to claim 1 selected from
4-[1-(4-fluoro-phenyl)-2-methyl-1H-imidazol-4-ylethynyl]-2-methyl-pyridine,
4-[1-(3,4-dichloro-phenyl)-2-methyl-1H-imidazol-4-yl-ethynyl]-2-methyl-pyridine hydrochloride,
4-[1-(2,4-difluoro-phenyl)-2-methyl-1H-imidazol-4-yl-ethynyl]-2-methyl-pyridine,
4-[1-(3,4-difluoro-phenyl)-2-methyl-1H-imidazol-4-yl-ethynyl]-2-methyl-pyridine, 2-methyl-4-[2-methyl-1-(3-trifluoromethyl-phenyl)-1H-imidazol-4-ylethynyl]-pyridine.

19. The compound according to claim 1 selected from
4-[1-(4-fluoro-phenyl)-2,5-dimethyl-1H-imidazol-4-yl-ethynyl]-2-methyl-pyridine, and
3-(4-fluoro-phenyl)-2-methyl-5-(2-methyl-pyridin-4-yl-ethynyl)-3H-imidazole-4-carbaldehyde.

20. The compound according to claim 1 selected from
4-[1-(4-chloro-phenyl)-2-methyl-1H-imidazol-4-ylethynyl]-2-methyl-pyridine,
4-[2-cyclopropyl-1-(4-fluoro-phenyl)-1H-imidazol-4-yl-ethynyl]-2-methyl-pyridine,
4-[1-(3-fluoro-phenyl)-2-methyl-1H-imidazol-4-ylethynyl]-2-methyl-pyridine,
4-[1-(3,5-difluoro-phenyl)-2-methyl-1H-imidazol-4-yl-ethynyl]-2-methyl-pyridine,
4-[1-(3-fluoro-4-methyl-phenyl)-2-methyl-1H-imidazol-4-ylethynyl]-2-methyl-pyridine,
4-[1-(3-chloro-4-fluoro-phenyl)-2-methyl-1H-imidazol-4-ylethynyl]-2-methyl-pyridine,
2-methyl-4-(2-methyl-1-p-tolyl-1H-imidazol-4-ylethynyl)-pyridine,
4-[1-(4-methoxy-phenyl)-2-methyl-1H-imidazol-4-yl-ethynyl]-2-methyl-pyridine,
2-methyl-4-[2-methyl-1-(4-trifluoromethyl-phenyl)-1H-imidazol-4-ylethynyl]-pyridine.

21. A composition comprising a compound of formula I

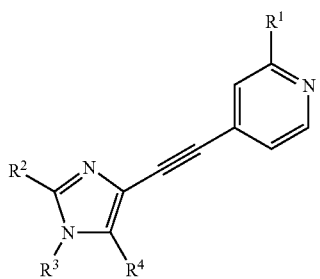

wherein
R$^1$ is C$_1$–C$_6$alkyl;
R$^2$ is C$_1$–C$_6$alkyl or C$_3$–C$_{12}$cycloalkyl;
R$^3$ is aryl that is unsubstituted or substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, heterocycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and
R$^4$ is hydrogen, C(O)H or CH$_2$R$^5$ wherein R$^5$ is hydrogen, OH, C$_1$–C$_6$alkyl or C$_3$–C$_{12}$cycloalkyl
and a pharmaceutically acceptable carrier.

22. A composition of claim 21 comprising a compound of formula I*

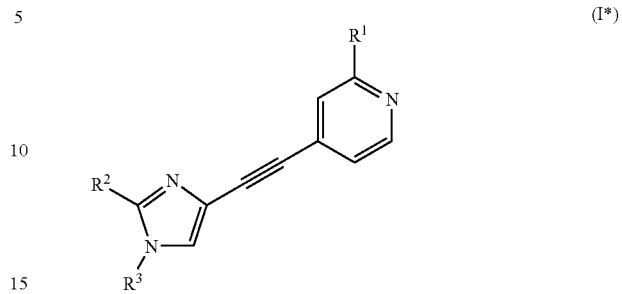

wherein
R$^1$ signifies lower alkyl;
R$^2$ signifies lower alkyl;
R$^3$ signifies aryl, optionally substituted, by one, two or three substituents, selected from the group consisting of halogen, lower alkyl, lower alkyl-halogen or cyano;
and a pharmaceutically acceptable carrier.

23. A process for the production of a compound of formula I

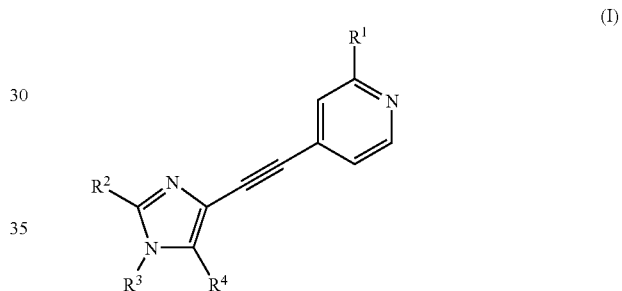

wherein
R$^1$ is C$_1$–C$_6$alkyl;
R$^2$ is C$_1$–C$_6$alkyl or C$_3$–C$_{12}$cycloalkyl;
R$^3$ is aryl that is unsubstituted or substituted by one, two or three substituents selected from halogen, C$_1$–C$_6$alkyl, S—C$_1$–C$_6$alkyl, C$_1$–C$_6$alkyl-halogen, C$_1$–C$_6$alkoxy, halogen-C$_1$–C$_6$alkoxy, C$_3$–C$_{12}$cycloalkyl, C$_1$–C$_6$alkylamino, di-C$_1$–C$_6$alkylamino, C$_1$–C$_6$alkoxyamino, (C$_1$–C$_6$alkoxy) C$_1$–C$_6$alkylamino, C$_3$–C$_{12}$cycloalkylamino, benzylamino and cyano; and
R$^4$ is hydrogen, C(O)H or CH$_2$R$^5$ wherein R$^5$ is hydrogen, OH, C$_1$–C$_6$alkyl or C$_3$–C$_{12}$cycloalkyl which process comprises reacting a compound of formula II

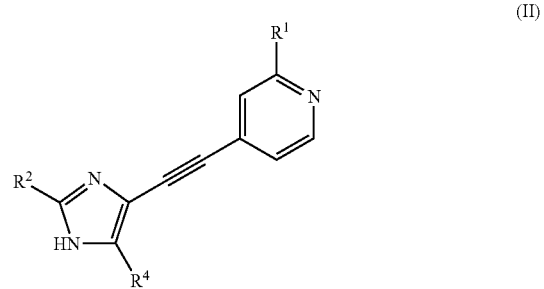

wherein $R^1$, $R^2$ and $R^4$ are as defined above,
with a compound of formula III $$R^3—Z \qquad (III)$$

wherein $R^3$ has the above meaning and Z is halogen or $B(OH)_2$.

24. A process for the production of a compound of formula I

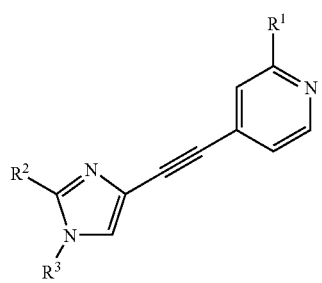

(I*)

wherein
$R^1$ is $C_1$–$C_6$alkyl;
$R^2$ is $C_1$–$C_6$alkyl or $C_3$–$C_{12}$cycloalkyl;
$R^3$ is aryl that is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
$R^4$ is hydrogen, C(O)H or $CH_2R^5$ wherein $R^5$ is hydrogen, OH, $C_{11}$–$C_6$alkyl or $C_3$–$C_{12}$cycloalkyl
which process comprises reacting a compound of formula IV

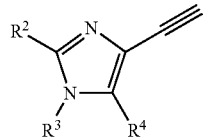

(IV)

wherein $R^2$, $R^3$ and $R^4$ have the meaning as defined above, with a compound of formula V

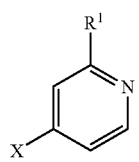

(V)

wherein $R^1$ has the above meaning and X is halogen.

25. A process for the production of a compound of formula I

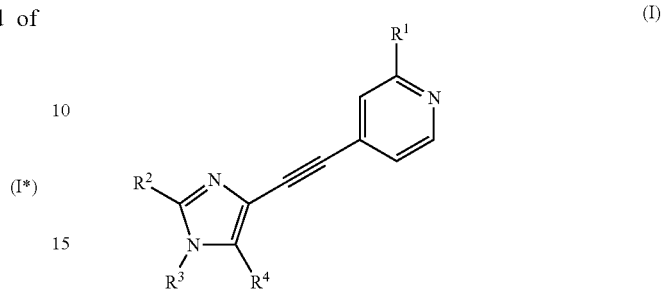

(I)

wherein
$R^1$ is $C_1$–$C_6$alkyl;
$R^2$ is $C_1$–$C_6$alkyl or $C_3$–$C_{12}$cycloalkyl;
$R^3$ is aryl that is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
$R^4$ is hydrogen, C(O)H or $CH_2R^5$ wherein $R^5$ is hydrogen, OH, $C_1$–$C_6$alkyl or $C_3$–$C_{12}$cycloalkyl
which process comprises reacting a compound of formula VI

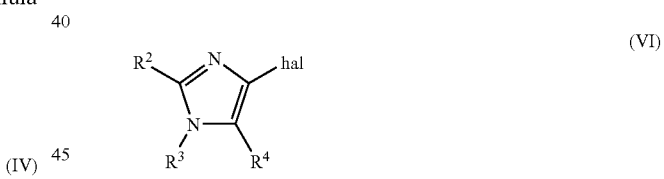

(VI)

wherein $R^2$, $R^3$ and $R^4$ have the meanings as defined above and hal is halogen,
with a compound of formula VII

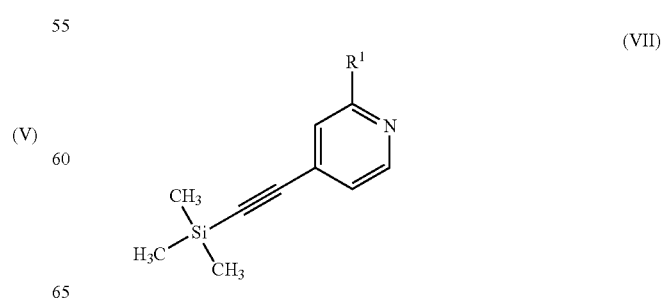

(VII)

wherein $R^1$ has the above meaning.

26. A method of treating anxiety comprising administering a therapeutically effective amount of a compound of formula I

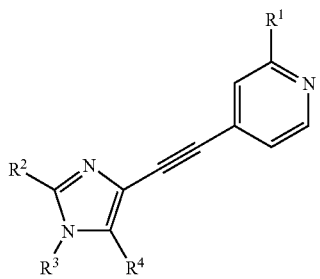

(I)

wherein
- $R^1$ is $C_1$–$C_6$alkyl;
- $R^2$ is $C_1$–$C_6$alkyl or $C_3$–$C_{12}$cycloalkyl;
- $R^3$ is aryl that is unsubstituted or substituted by one, two or three substituents selected from halogen, $C_1$–$C_6$alkyl, S—$C_1$–$C_6$alkyl, $C_1$–$C_6$alkyl-halogen, $C_1$–$C_6$alkoxy, halogen-$C_1$–$C_6$alkoxy, $C_3$–$C_{12}$cycloalkyl, $C_1$–$C_6$alkylamino, di-$C_1$–$C_6$alkylamino, $C_1$–$C_6$alkoxyamino, ($C_1$–$C_6$alkoxy) $C_1$–$C_6$alkylamino, $C_3$–$C_{12}$cycloalkylamino, benzylamino and cyano; and
- $R^4$ is hydrogen, C(O)H or $CH_2R^5$ wherein $R^5$ is hydrogen, OH, $C_1$–$C_6$alkyl or $C_3$–$C_{12}$cycloalkyl.

27. The method of claim 26 wherein the compound is a compound of formula I*

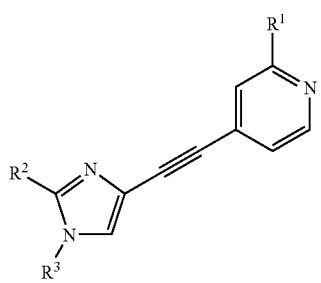

(I*)

wherein
- $R^1$ signifies lower alkyl;
- $R^2$ signifies lower alkyl;
- $R^3$ signifies aryl, optionally substituted, by one, two or three substituents, selected from the group consisting of halogen, lower alkyl, lower alkyl-halogen or cyano.

* * * * *